(12) United States Patent
Hellerstein et al.

(10) Patent No.: US 8,883,847 B2
(45) Date of Patent: Nov. 11, 2014

(54) COMPOSITIONS AND METHODS OF TREATMENT USING MODULATORS OF MOTONEURON DISEASES

(75) Inventors: Marc K. Hellerstein, Kensington, CA (US); Patrizia A. Fanara, Oakland, CA (US)

(73) Assignee: KineMed, Inc., Emeryville, CA (US)

( * ) Notice: Subject to any disclaimer, the term of this patent is extended or adjusted under 35 U.S.C. 154(b) by 398 days.

(21) Appl. No.: 11/650,020

(22) Filed: Jan. 5, 2007

(65) Prior Publication Data

US 2007/0238773 A1    Oct. 11, 2007

Related U.S. Application Data

(60) Provisional application No. 60/756,836, filed on Jan. 5, 2006, provisional application No. 60/756,952, filed on Jan. 5, 2006.

(51) Int. Cl.

| | | |
|---|---|---|
| *A61K 31/353* | (2006.01) | |
| *A61K 31/55* | (2006.01) | |
| *A61P 25/14* | (2006.01) | |
| *A61P 25/16* | (2006.01) | |
| *G01N 33/68* | (2006.01) | |
| *A61K 31/35* | (2006.01) | |
| *A61K 31/4748* | (2006.01) | |
| *C07D 407/04* | (2006.01) | |
| *A61K 31/4741* | (2006.01) | |
| *A61K 31/40* | (2006.01) | |
| *A61K 45/06* | (2006.01) | |

(52) U.S. Cl.
CPC ............ *G01N 33/6896* (2013.01); *A61K 31/35* (2013.01); *A61K 31/4748* (2013.01); *C07D 407/04* (2013.01); *A61K 31/4741* (2013.01); *A61K 31/40* (2013.01); *A61K 45/06* (2013.01)
USPC ........................ 514/454; 514/280; 514/211.01

(58) Field of Classification Search
USPC .......... 514/410, 411, 422, 454, 269.7, 71, 90, 514/385, 355, 280, 211.01
See application file for complete search history.

(56) References Cited

U.S. PATENT DOCUMENTS

| | | | | |
|---|---|---|---|---|
| 4,818,539 | A * | 4/1989 | Shaw et al. ..................... | 424/441 |
| 5,229,394 | A * | 7/1993 | Salazar-Grueso ............. | 514/289 |
| 5,780,489 | A * | 7/1998 | Brooks ........................ | 514/369 |
| 6,524,629 | B1 * | 2/2003 | Christen ...................... | 424/752 |
| 7,572,762 | B1 | 8/2009 | Spruce et al. | |
| 2003/0166670 | A1 | 9/2003 | Brooks-Korn | |
| 2003/0228259 | A1 | 12/2003 | Hellerstein | |
| 2006/0020440 | A1 | 1/2006 | Hellerstein | |
| 2008/0014267 | A1 | 1/2008 | Giordano et al. | |

FOREIGN PATENT DOCUMENTS

| | | |
|---|---|---|
| JP | A2001-72589 | 3/2001 |
| JP | A2002-522387 | 7/2002 |
| JP | A2003-525854 | 9/2003 |
| WO | WO 2004/078144 | 9/2004 |
| WO | WO 2005/081943 A2 | 9/2005 |
| WO | WO 2005/115372 | 12/2005 |
| WO | WO 2006/017812 A1 | 2/2006 |
| WO | WO 2006/091728 A | 8/2006 |
| WO | WO 2007/081910 A2 | 7/2007 |

OTHER PUBLICATIONS

Argyriou, A.A. et al., 2005, "Vitamin E for prophylaxis against chemotherapy-induced neuropathy: a randomized controlled trial.", *Neurology*, vol. 64, No. 1, pp. 26-31.

Bruce, K.M. et al., 2004, "Chemotherapy delays progression of motor neuron disease in the SOD1 G93A transgenic mouse", vol. 50, No. 3, pp. 138-142.

Kozhevnikova, E.V. et al., 1999, "Neuroprotective activity of angiotensin-converting enzyme inhibitors during cerebral ischemia", *Bulletin of Experimental Biology and Medicine*, vol. 128, No. 5, pp. 1122-1124.

Landen, J. et al., 2004, "Noscapine crosses the blood-brain barrier and inhibits glioblastoma growth", *Clinical Cancer Research*, vol. 10, No. 15.

Landen, J., et al., 2002, "Noscapine alters microtubule dynamics in living cells and inhibits the progression of melanoma", vol. 62, No. 14, pp. 4109-4114.

Mooraki, A., et al., 2005, "Noscapine suppresses angiotensin converting enzyme inhibitors-induced cough", *Nephrology*, vol. 10, No. 4, pp. 348-350.

Stubblefield, M.D. et al., 2005, "Glutamine as a Neuroprotective Agent in High-dose Paclitaxel-induced Peripheral Neuropathy: A Clinical and Electrophysiologic Study", *Clinical Oncology*, vol. 17, No. 4, pp. 271-276.

(Continued)

*Primary Examiner* — Sreeni Padmanabhan
*Assistant Examiner* — Sahar Javanmard
(74) *Attorney, Agent, or Firm* — Moran, Lewis & Bockius LLP

(57) ABSTRACT

The invention disclosed herein describes a novel therapeutic target for motoneuron diseases (altered dynamics of microtubules in neurons); a method for measuring the state of activity of this therapeutic target in subjects with established, incipient, or potential motoneuron disease; the discovery of drug agents that modulate neuronal microtubule dynamics in living subjects with motoneuron diseases; the discovery that administration of such agents, alone or in combinations, can provide marked neuroprotective therapy for living subjects with motoneuron diseases including delay in symptoms and prolongation of survival; and the discovery that monitoring of neuronal microtubule dynamics in subjects with motoneuron diseases, in response to therapeutic interventions, allows diagnostic monitoring for optimization of therapeutic regimen and strategy for individual subjects or for drug trials.

8 Claims, 25 Drawing Sheets

(56) References Cited

OTHER PUBLICATIONS

Baqri, R. et al. "Kinesin-2 Differentially Regulates the Anterograde Axonal Transports of Acetylcholinesterase and Choline Acetyltransferase in *Drosophila*", 2006, *J. Neurobiology*, vol. 66, No. 4, pp. 378-392.

Ratner, N. et al. "A Role for Cyclin-Dependant Kinase(s) in the Modulation of Fast Anterograde Axonal Transport: Effects Defined by Olomoucine and the APC Tumor Suppressor Protein" 1998, *J. Neuroscience*, vol. 18(19):7717-1726.

Van Laar, J.M. et al., Tweaking Microtubles to Treat Scleroderma, *PLOS Medicine*, (2005) vol. 2, p. 1230-1231.

Zeeberg B. et al., 1980, "Exchange of tuburlin dimer into rings in microtuble assembly-dissasemnly." *Biochemistry* vol. 19, No. 22, pp. 5078-5086.

Fanara, Patrizia et al., 2004, "In vivo measurement of microtuble dynamics using stable isotope labeling with heavy water. Efect of taxanes." *Journal of Biological Chemistry* vol. 279, No. 48, pp. 49940-49947.

Fanara et al., "Stabilization of Hyperdermic Microtubles is Neuroprotective in Mayotrophic Lateral Sclerosis" *J. Bio. Chem.*, vol. 282, No. 32, pp. 23465-23472, 2007.

Feit, Howard et al., "Is Tubulin a Glycoprotein?" Biochem Biophys Res Comm 66:, No. 3, 1975, pp. 920-927.

Trojanowski, John Q. et al., "Microtuble-stabilising drugs for therapy of Alzheimer's disease and other neurodegenerative disorders with axonal transport impairments." *Expert Opin. Pharmacother.* (2005) 6(5):683-686.

Wacker, Irene et al., "Microtuble-dependent transport of secretary vesicles visualized in real time with a GFP-tagged secretory protein", *J. of Cell Science* 110, 1453-1463 (1997).

Hino, Mizuki, "Glycosylation of the Alpha and Beta Tubulin by Sialyioligosaccharides", *Zoological Science* 20: 709-715 (2003).

Galbraith, J.A. et al., "Axonal transport of tubulin and actin," *Journal of Neurocytology*, 2000, vol. 29, pp. 889-911.

* cited by examiner

Motoneuron Disease (MD) Drug Development Process

| Treatment Starts at 70 days | Onset of Symptoms | Delay in Onset | Survival | Delay in Mortality |
|---|---|---|---|---|
| *KineMed:* Untreated | 87.5±4.2 (mean±SD) | N/A | 118.5±4.2 (mean±SD) | N/A |
| *KineMed:* MTMA/KM-ID05 (Preclinical) (2006-present) | 120.1±9.3 (mean±SD) | 32.6 days | 144.1±8.6 (mean±SD) | 25.6 days |
| *KineMed:* MTMA/KM-ID06 (Preclinical) (2006-present) | 123.9±5.7 (mean±SD) | 36.4 days | 149.7±7.1 (mean±SD) | 31.2 days |
| *KineMed:* MTMA/KM-ID07 (Preclinical) (2006-present) | 126.2±4.7 (mean±SD) | 38.7 days | 153.5±5.6 (mean±SD) | 35 days |

| Treatment Initiated Before Onset (49 days) | Delay in Disease Progression | Delay in Mortality |
|---|---|---|
| Aventis Rilutek® (Riluzole) FDA approved in 1995 | 9.7 days | 12 days |

FIG. 21

COMPOSITIONS AND METHODS OF TREATMENT USING MODULATORS OF MOTONEURON DISEASES

CROSS REFERENCE TO RELATED APPLICATIONS

The present invention claims the benefit of priority under 35 U.S.C. §119(e) to U.S. Provisional Application Nos. 60/756,836, filed Jan. 5, 2006 and 60/756,952, filed Jan. 5, 2006, all hereby incorporated by reference in their entirety.

FIELD OF INVENTION

The present invention relates to novel pharmaceutical compounds that affect motoneuron activity and dynamicity. The invention further relates to use of such novel pharmaceutical compounds in the treatment of motoneuron disorders such as amyotrophic lateral sclerosis. The invention further relates to screening and monitoring test subjects for the presence of such motoneuron disorders.

BACKGROUND OF THE INVENTION

The motoneuron diseases are a group of progressive neurological disorders that damage or destroy motor neurons, the cells that control voluntary muscle activity such as speaking, walking, breathing, and swallowing. Characteristic symptoms of motoneuron diseases include progressive weakness; loss of strength and loss of muscle mass (wasting); involuntary movements including twitching of muscles; spasticity or stiffness in the arms and legs; and overactive tendon reflexes. Other symptoms of motoneuron diseases can include slowing of voluntary movements (bradykinesias), lack of movement (hypokinesia, masked faces), stereotypical and repeated involuntary movements (choreoathetosis), and frozen postures or restlessness (akathisia). Sensation, intellect, memory, and personality are not affected in pure motoneuron diseases. In some types of motoneuron diseases, such as amyotrophic lateral sclerosis (ALS, commonly called Lou Gehrig's disease), muscle weakness is progressive and eventually leads to death, typically associated with loss of respiratory muscle function. Other types of motoneuron diseases progress slowly over the course of many years.

Motoneuron diseases occur in adults and children, and are more common in men than in women. In adults, symptoms usually appear after age 40, and may be non-specific, making diagnosis difficult. In children, particularly in inherited forms of the disease, symptoms may be present from birth. Inherited forms of motoneuron diseases are caused by genetic mutations or deletions that cause degeneration of motor neurons. Hereditary motoneuron diseases include a group of childhood disorders known as the spinal muscular atrophies. Nonhereditary (also called sporadic) motoneuron diseases are caused by unknown factors, although environmental toxins or viruses may act as disease triggers. Nonhereditary motoneuron diseases include ALS (although some hereditary forms do exist), progressive bulbar palsy, pseudobulbar palsy, primary lateral sclerosis, progressive muscular atrophy, Parkinson's disease, diabetic neuropathy, post-polio syndrome and many others. There are no specific laboratory tests to diagnose the motoneuron diseases.

ALS is an inexorably progressive, invariably fatal disease of the peripheral nervous system. Specifically, ALS is a disease of motor neurons characterized by dysfunction of axons. There is currently no effective treatment. Riluzole (Rilutek®) was approved by the FDA in 1995 but only delays disease progression modestly. In addition to nonhereditary ALS, hereditary forms of ALS exist. Up to 20% of patients with familial ALS have a mutation in the superoxide dismutase (SOD1) gene. This finding allowed the development of a faithful mouse model for ALS. This model, the SOD1-G93A transgenic mouse ("SOD1-G93A TGN mouse"), develops a neurological disorder that mimics ALS and results in death by 18-19 weeks of age.

The SOD1-G93A TGN mouse has become very useful for preclinical discovery and testing of drugs. This particular transgenic mouse model of ALS exhibits higher expression of mutant human Cu,Zn SOD and a shorter course of disease (18-19 weeks). Evaluation of potential therapeutic agents is thereby made faster and more efficient. Also, demonstration of therapeutic benefit in this more aggressive (i.e., high expression) mouse model may provide the most stringent criterion for predicting success in the clinic. Given the expense and time required to organize human clinical trials, only the most active and potent candidate drugs should be brought forward for evaluation in patients. A variety of potential therapeutic agents has been tested in the SOD1-G93A TGN mouse. Other treatment methodologies also have been tested in this model, such as transplantation with human neural stem cells. All treatment modalities tested to date, including Riluzole and neural stem cell transplantation, only delay disease onset and mortality by 20 to 30 days in this model.

The relative lack of success of candidate agents in the SOD1-G93A TGN mouse may reflect the fundamental lack of understanding of the underlying mechanism of motoneuron diseases. More effective treatments for motoneuron diseases might be discovered and developed if underlying molecular targets and pathways involved in disease progression were known.

U.S. Provisional Applications Nos. 60/722,897, PCT/US2005/028069 and U.S. patent application Ser. No. 10/279,399, are all hereby incorporated by reference in its entirety.

SUMMARY OF THE INVENTION

Accordingly, in one aspect the invention provides pharmaceutical compositions comprising a first neuroprotective agent and second neuroprotective agent. Usually, at least one of the neuroprotective agents is a microtubule target modulating agent (MTMA) such as noscapine. Sometimes the pharmaceutical composition comprises only one neuroprotective agent, particularly a microtubule target modulating agent (MTMA) such as noscapine. Sometimes the pharmaceutical composition comprises three neuroprotective agents, particularly wherein one or two of the neuroprotective agents are MTMAs. Neuroprotective agents are selected from MTMAs; anti-inflammatory agents including thiazolidinedione and nonthiazolidinedione peroxisome proliferator-activated receptor gamma (PPARγ) agonists; ion channel modulators including selective and nonselective glutamate receptor antagonists such as antagonists for voltage gated ion channels, including voltage gated sodium channel (VGNH) and a voltage gated calcium channel (VGCH) such as N-methyl-D-aspartate (NMDA) receptor; α-amino-3-hydroxy-5-methyl-4-isoxazolepropionic acid (AMPA) antagonists; glial modulators; low-voltage sensitive calcium channel (L-VSCCS) blockers; N-type and P/Q type voltage dependent calcium current inhibitors; CB1 receptor and CB2 receptor agonists such as cannabinoids including endocannabinoid and cannabinoid receptor agonist; AEA transport, hydrolysis and reuptake inhibitors including fatty acid amidohydrolase (FAAH) inhibitor; antioxidants such as inducible nitric oxide synthase (iNOS) inhibitors, free radical trappers/scavengers, and metal ion chelators including copper(II) and zinc(II) chelators; neurotrophic factors; and apoptosis inhibitors. Each neuroprotective agent of a composition may be in vials separate from the others.

In an additional aspect, the invention provides methods of treating motoneuron disease comprising administering a pharmaceutical composition comprising one, two, three or more neuroprotective agents. The pharmaceutical composition may further comprise a pharmaceutical carrier.

In a further aspect, the invention provides methods of treating ALS comprising administering a pharmaceutical composition comprising one, two, three or more neuroprotective agents. The pharmaceutical composition may further comprise a pharmaceutical carrier. Such treatment may result in delayed onset of ALS symptoms or reduction in severity of ALS symptoms.

In an additional aspect, the invention provides methods of ameliorating symptoms of ALS in a patient comprising administering an MTMA and a pharmaceutical carrier to the patient.

In a further aspect, the invention provides methods of treating a motoneuron disease comprising administering to a patient in need thereof a therapeutically effective amount of an MTMA and a pharmaceutical carrier to the patient.

In a further aspect, the invention provides methods for monitoring the effects of an agent in subjects with a motoneuron disease. The methods comprise exposing a test living system to one or more agents and administering an isotope-labeled substrate to the living system for a period of time sufficient for the isotope-labeled substrate to enter into one or more tubulin subunits and thereby enter into and label one or more microtubule molecules. A first sample comprising motoneurons is then obtained from the living system, and the isotopic enrichment of subpopulations of microtubules from the first sample is quantified. The isotopic enrichment of subpopulations of microtubules from a control system is either quantified or provided, and the ratio of enrichments in the microtubules in the living system is compared to the ratio in a control living system to determine the effect of the agent on microtubule labeling in motoneurons.

In a further aspect, the method further comprises calculating the dynamicity of the labeled microtubules, wherein the comparing step comprises calculating the ratio of isotopic enrichment or dynamicity in the microtubules to the isotopic enrichment of free tubulin and comparing the ratio to the same ratio in the control living system.

In an additional aspect, the method comprises comparing the isotopic enrichment or dynamicity of microtubules from growth cone microtubules from the test living system to the isotopic enrichment or dynamicity of labeled microtubules from growth cone microtubules from the control living system.

In a further aspect, the method utilizes comparing the isotopic enrichment or dynamicity of microtubules from axonal microtubules from the test living system to the isotopic enrichment of microtubules from axonal microtubules from the control living system.

In an additional aspect, the agent to which a test living system is exposed is a neuroprotective factor. The agent can be administered alone or in combination with other agents.

In a further aspect, the invention provides methods of treating a motoneuron disease by administering an agent that alters neuronal microtubule dynamicity.

In an additional aspect, the invention provides methods of screening for agents effective in motoneuron disease comprising contacting neurons with an agent that alters microtubule dynamicity.

In a further aspect, the invention provides methods of diagnosing or monitoring the effects of therapy in subjects with a motoneuron disease, comprising administering an isotope-labeled substrate to the living system for a period of time sufficient for the isotope-labeled substrate to enter into one or more tubulin subunits and thereby enter into and label one or more microtubule polymer molecules, and obtaining a first sample comprising motoneurons from the living system. The isotopic enrichment of subpopulations of microtubules in the axonal compartment from the first sample are quantified as well as the isotopic enrichment of subpopulations of unincorporated labeled tubulin from the axonal compartment. The ratio of enrichments of the subpopulations of microtubules in the axonal compartment is compared to the ratio of said subpopulations of unincorporated labeled tubulin from the axonal compartment to determine the presence of a motoneuron disease.

In a further aspect, the invention provides methods for evaluating and monitoring therapeutic efficacy of candidate agents being tested in clinical trials in subjects with motoneuron diseases, comprising administering an isotope-labeled substrate to a living system for a period of time sufficient for the isotope-labeled substrate to enter into one or more tubulin subunits and thereby enter into and label one or more microtubule polymer molecules and obtaining a first sample comprising motoneurons from the living system. The isotopic enrichment of subpopulations of microtubules in the axonal compartment from the first sample are quantified as well as the isotopic enrichment of subpopulations of unincorporated labeled tubulin from the axonal compartment. The ratio of enrichments of the subpopulations of microtubules in the axonal compartment is compared to the ratio of said subpopulations of unincorporated labeled tubulin from the axonal compartment to determine the presence of a motoneuron disease. Different treatment groups are compared statistically to evaluate the therapeutic efficacy of said candidate agents and repeat measurements and analyses can be done to monitor therapeutic activity or changes in efficacy of said candidate agents over the time of treatment.

BRIEF DESCRIPTION OF THE DRAWINGS

FIG. 21. Selected potential clinical agents from ALS-SOD1 animal studies compared to the FDA approved drug Rilutek®

DETAILED DESCRIPTION OF THE INVENTION

Figure 1A:
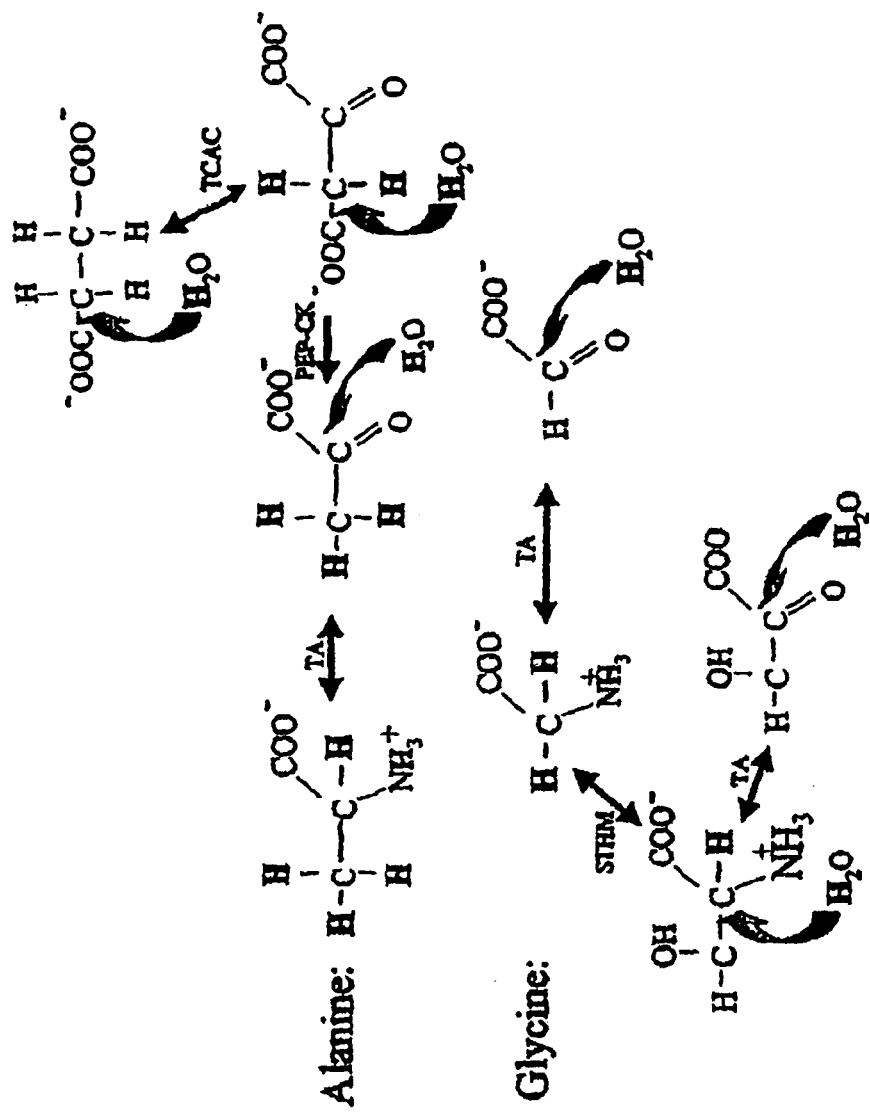
FIGS. 1A and 1B depict pathways of labeled hydrogen ($^2$H or $^3$H) exchange from isotope-labeled water into selected free amino acids. Two NEAA's (alanine, glycine) and an EAA (leucine) are shown, by way of example. Alanine and glycine are presented in FIG. 1A. Leucine is presented in FIG. 1B. Abbreviations: TA, transaminase; PEP-CK, phosphoenolpyruvate carboxykinase; TCAC, tricarboxylic acid cycle; STHM, serine tetrahydrofolate methyltransferase.

Biochemistry and Cell Biology of Motoneurons and Motoneuron Diseases

The highly asymmetric morphology of neurons, characterized by the presence of axodendritic processes that can reach in length several orders of magnitude the diameter of the cell body, is determined by the capacity of the cytoskeleton to sustain such processes and to support the transport of organelles, vesicles, or protein subunits and complexes over very long distances. One of the major cytoskeletal systems is the microtubule-based transport system along which kinesin and dynein motor proteins generate force and drive the traffic of many cellular components. Materials such as neurotransmitter peptides are synthesized in the cell body and sequestered in vesicles at the golgi. These vesicles are then transported down the axon towards the synapse by kinesin motor proteins. Other materials are transported from the synapse to the cell body by dynein motors. Motoneuron diseases, like ALS, various neuropathies including diabetic neuropathy, and Parkinson's disease, share major pathophysiological cellular changes such as impaired axonal transport, followed by axonal loss and consequent neuronal atrophy.

Microtubules ("MTs") are very abundant in neurons where they facilitate the formation of, and confer stability to, neurites (axons and dendrites). They are the primary determinant of neuronal morphology and facilitate the formation of, and confer stability to, neurites (axons and dendrites). The process of assembly and disassembly of axonal microtubules (known as "microtubule dynamics") underlies their ability to determine and maintain neuronal morphology. This process, essential for the structural stability of the neuron, also represents a signaling pathway within neurons. Microtubule dynamics is regulated largely by microtubule-associated proteins (MAPs). The neuronal MAPs have a specific polar distribution and play a prominent role in the stabilization of microtubules.

Neurons such as motor neurons have several distinct populations of neuronal microtubules, generally classified by the MAPs to which they bind. By "neuronal microtubules" is meant a protein structure composed of polymers of tubulin, occurring singly, in pairs, triplets or bundles in living cells. By "tubulin" is meant the principal protein component of microtubules. Tubulin is a dimer composed of two globular polypeptides, alpha-tubulin and beta-tubulin (α- and β-tubulin). Microtubules are assembled from dimers α- and β-tubulin.

Neuronal microtubules are present in different neuronal compartments (e.g., soma, dendrites and axons) and in association with different MAPs (e.g., tau, MAP2 and STOP). Microtubules are required to establish and maintain neuronal differentiation and long-distance transport of neurotransmitter substances along the axons to distant synapses.

In general, there are three main classes of neuronal microtubules: growth cone (also known as "axonal distal" or "axonal tip") microtubules (also referred to herein and in the figures as "tau-MTs"); dendritic microtubules (also referred to herein as "MAP-2 MTs"), and hillock and axonal shaft microtubules (also referred to herein and in the figures as "STOP-MTs"). In general, the terminology arises from the microtubule-associated proteins that bind each category. "MAPs" or "microtubule-associated proteins" are proteins that, upon binding to a microtubule, alter its function and/or behavior. Thus, for example, capture of growth cone and axonal distal microtubules is done by using affinity binding to tau antibody. The tau-unbound material (the dendritic microtubules) is then captured by affinity binding to MAP2 antibody, leaving only hillock and axonal shaft microtubule (STOP-MTs) in the MAP2-unbound fraction. Alternatively, STOP-MTs can be directly isolated by exploiting their unique ability, compared to other MT subpopulations, to resist depolymerization in cold temperatures and millimolar concentration of $CaCl_2$.

As used herein, "tau" or "tau protein" or "tau MAP" is a major class of microtubule-associated proteins (MAPs) isolated from the brain. In nerve cells tau is highly enriched in the axonal growth cone. Tau proteins promote the nucleation (initiation) process of tubulin polymerization in vitro. Tau is known to be a regulator of the turnover/assembly of dynamic axonal growth cone microtubules in the brain. Chemically modified tau proteins also appear to be involved in the formation and/or composition of the neurofibrillary tangles and neuropil threads found in Alzheimer's disease.

As used herein, "MAP2" or "Microtubule-Associated Protein-2" is a high molecular weight microtubule-associated protein that is highly enriched in neuronal dendritic microtubules. Under certain conditions, MAP2 is required for tubulin assembly into microtubules and stabilizes the assembled microtubules, regulating their dynamics.

As used herein, "STOP" or "Stable Tubule Only Polypeptide" is a neuronal $Ca^{2+}$ calmodulin-regulated microtubule associated protein. STOP stabilizes microtubules indefinitely against in vitro disassembly induced by cold temperature, millimolar calcium or drugs.

By "neuronal cold-stable microtubules" is meant an abundant subpopulation of axonal microtubules that are stable to disassembly induced by both drugs and cold-temperature. Resistance to microtubule disassembly by drugs and cold-temperature is largely due to polymer association with STOP.

Overview of the Invention

The invention disclosed herein relates to: (1) the discovery of a novel therapeutic target for motoneuron diseases—namely, the dynamicity of neuronal microtubules (i.e., the rate of assembly and disassembly of specific subpopulations of microtubules from tubulin dimers)—by use of novel isotope labeling techniques for direct measurement of microtubule dynamics; (2) the discovery that the dynamicity of neuronal microtubules can be measured in living animals or human subjects by use of isotope labeling techniques and is markedly altered in motoneuron diseases such as ALS, even before the manifestation of physical symptoms or neurological loss of function in the animal or human subject; (3) the finding that the altered dynamicity of neuronal microtubules in motoneuron diseases such as ALS can be modulated by administration of certain drugs including, but not limited to noscapine, nocodazole, taxanes and other agents given alone or in combination with agents that target other neuronal systems, receptors, or pathways; (4) the discovery that administration of agents that modulate the dynamics of microtubules in neurons, alone or in combinations of agents, to animals or human subjects with established or incipient motoneuron diseases such as ALS can markedly delay or prevent the loss of neurologic function in the motoneuron diseases, including delayed onset of signs and symptoms of motoneuron diseases, slowing of progression of the signs and symptoms and delay in time to death (i.e., prolongation of survival), thereby representing successful neuroprotective therapy; (5) the discovery that monitoring of neuronal microtubule dynamics in animals or human subjects with established or incipient motoneuron diseases such as ALS, in response to administration of agents intended to provide neuroprotective therapy allows identification of the optimal dose, drug, combination of drugs, regimen, timing of therapy, duration of therapy, or other aspects of the optimal therapeutic strategy in individual subjects or in drug trials of subjects with motoneuron diseases (i.e., diagnostic monitoring).

In summary, the invention disclosed herein describes a novel therapeutic target for motoneuron diseases (altered dynamics of microtubules in neurons); a method for measuring the state of activity of this therapeutic target in subjects with established, incipient, or potential motoneuron disease; the discovery of drug agents that modulate neuronal microtubule dynamics in living subjects with motoneuron diseases; the discovery that administration of such agents, alone or in combinations, can provide marked neuroprotective therapy for living subjects with motoneuron diseases including delay in symptoms and prolongation of survival; and the discovery that monitoring of neuronal microtubule dynamics in subjects with motoneuron diseases, in response to therapeutic interventions, allows diagnostic monitoring for optimization of therapeutic regimen and strategy for individual subjects or for drug trials.

The use of neuroprotective strategies in ALS has considerable appeal. To date, however, there have been inherent problems with this approach, including the lack of a means for identifying patients at risk for ALS; the absence of a laboratory marker reflective of preclinical disease activity; the lack of proven neuroprotective agents; and the inability to know the optimal timing, dose or regimen of therapy. The lack of specific biochemical markers for sporadic and most types of familial ALS also has precluded preclinical identification of those individuals who are at risk. The present invention discloses biochemical measurements of abnormal microtubule dynamics in a well-established animal model of ALS (the SOD1-G93A TGN mouse) that have demonstrated for the first time that the true biochemical onset of the disease predates development of clinical deficits. Accordingly, measurement of neuronal microtubule dynamics may provide a "therapeutic window" for the use of neuroprotective compounds to prevent the final cascade of events leading to neuronal death. Because of the multifactorial downstream pathogenic pathways activated motoneuron diseases such as ALS, combinatorial approaches may be necessary to delay the rate of disease progression and prolong survival.

The present invention is directed to the discovery that neuronal microtubule dynamics are markedly altered in motoneuron diseases such as ALS and that by modulating the microtubule dynamics of hillock and axonal shaft (structural) microtubules, loss of motoneuron function can be minimized in subjects with incipient, established or potential motoneuron disease. This leads to a variety of applications, including compositions for use in treating motoneuron diseases, as well as methods for screening candidate agents and optimizing therapeutic regimens (e.g., through diagnostic monitoring) for the ability to modulate microtubules, motoneurons and motoneuron diseases. In addition, the present invention is directed to the modulation of motoneuron function and disease using a plurality of compositions that act at different points in motoneuron physiology, and thus synergistically act to preserve motoneuron function.

Accordingly, the present invention also is directed to compositions and methods for screening candidate agents for the ability to modulate microtubule dynamics in motoneurons. In addition, the invention provides compositions, both single compounds and combinations of compounds, to treat, ameliorate or prevent motoneuron diseases.

The present invention is based on measuring, for the first time, the rate of assembly and breakdown of the largely extended and stable microtubule polymers present in peripheral nerves of living animals or human subjects with motoneuron diseases. Without being bound by theory, it appears that some motoneuron diseases result from the dysfunction of the crucial intracellular cytoskeletal components responsible for the transportation of nutrients and other critical elements along the axonal process. The discovery disclosed herein, by use of a novel isotope/mass spectrometric technique for directly measuring neuronal microtubule dynamics in peripheral nerves of animals with motoneuron disease, of markedly increased turnover of microtubule polymers (i.e., a constant state of being degraded and rebuilt) in the axonal process, appears to disrupt the flow of molecules (including nutrients and other constituents necessary to maintain the stability of the axonal process itself). Accordingly, Applicants disclose here the discovery of a new and fundamental mechanism— namely, increased turnover of microtubules responsible for the stability of the axonal process (or "axonal projection")—documented in living subjects with motoneuron diseases for the first time—axonal instability and the resulting symptomatology associated with motoneuron diseases.

Figure 1B:
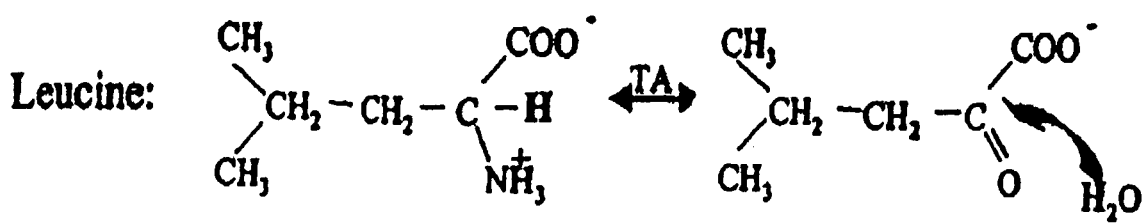
Figure 1C:
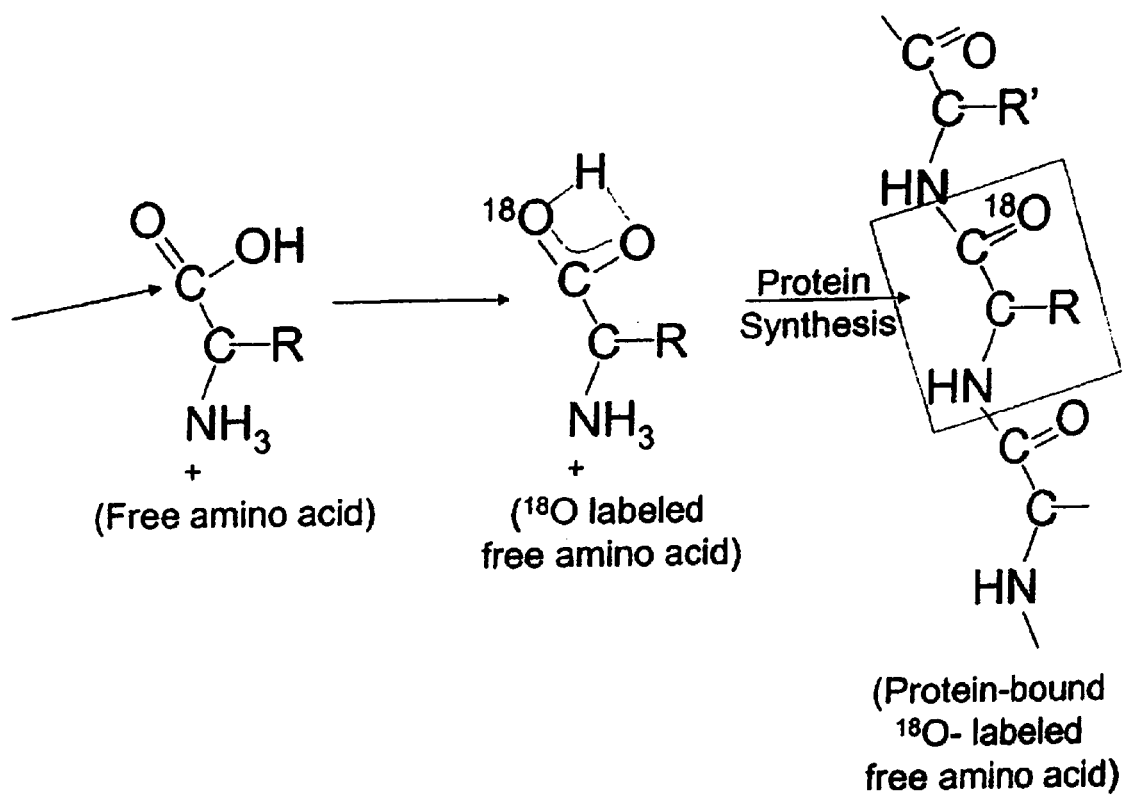
FIG. 1C depicts $^{18}$O-labeling of free amino acids by $H_2^{18}O$ for protein synthesis.
Figure 3:
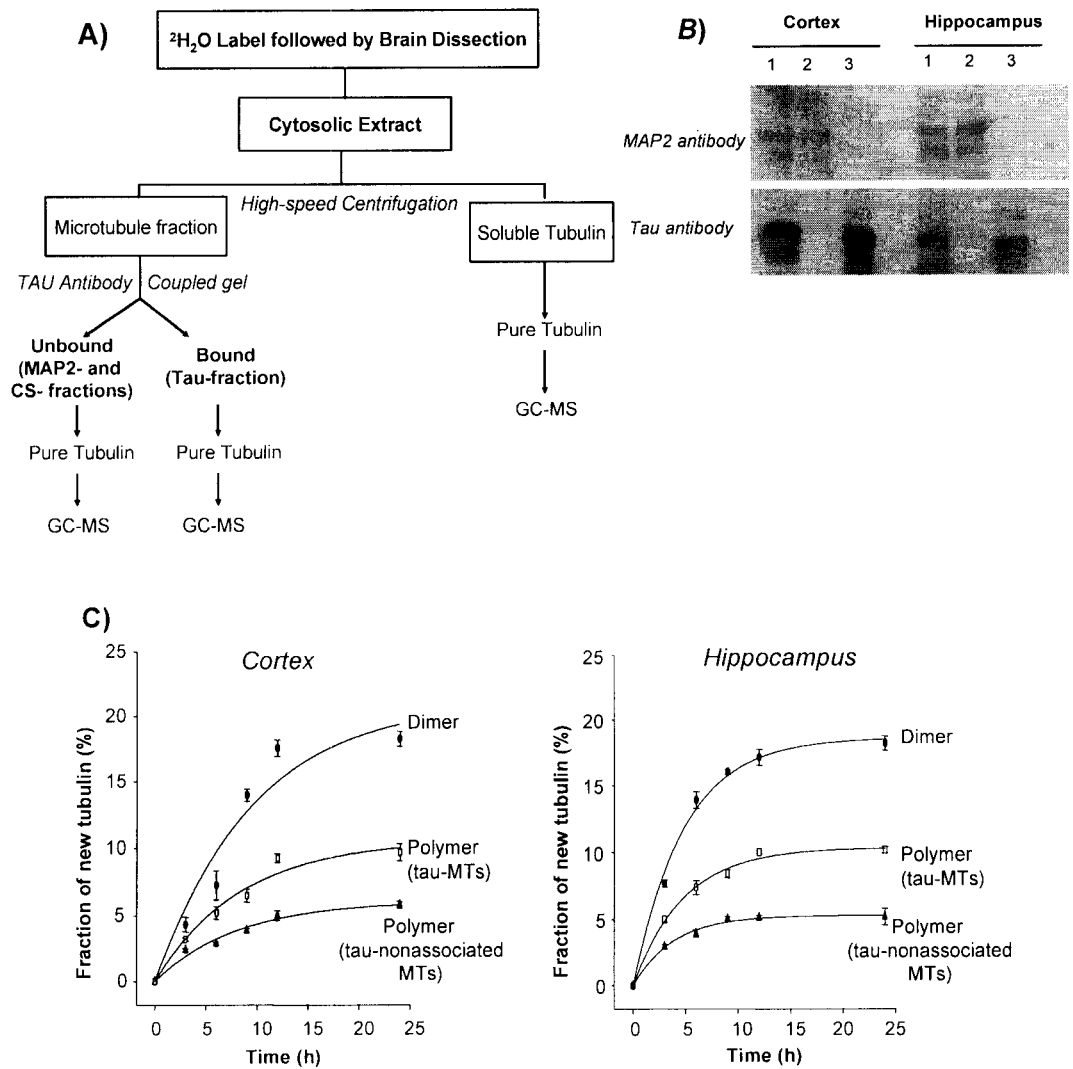
FIG. 3. In vivo exchange of tubulin dimers and microtubules in mouse brain. (A) Schematic representation of the strategy for isolating neuronal microtubule (MT) populations. (B) Anti-tau and anti-MAP2 Western blots of input (lane 1), tau-nonassociated (lane 2), and tau-associated (lane 3) fractions, separated over anti-tau columns, show quantitative capture of tau-associated MTs; MAP2-associated MTs are in the unbound fraction. (C) Kinetics of $^2$H incorporation from heavy water ($^2H_2O$) into tubulin dimers and different MT fractions. Mice were labeled with ca. 5% $^2H_2O$ in body water for various times, brains were dissected, and MT populations, isolated as in (A), were hydrolyzed. $^2H$ incorporation into C—H bonds of alanine was measured by NCI-GC/MS (mean±S.D.; n=3) and expressed as fractional turnover (% of alanine newly synthesized during the labeling period). Single-exponential curve fits are shown with $t_{1/2}$ ca. 5-6 hours in cortex and $t_{1/2}$ ca. 3 hours in hippocampus, leveling off at ca. 20% new alanine for tubulin dimers, or half or one-third of this value, respectively, for tau- and MAP2/STOP-MTs.
Figure 4:
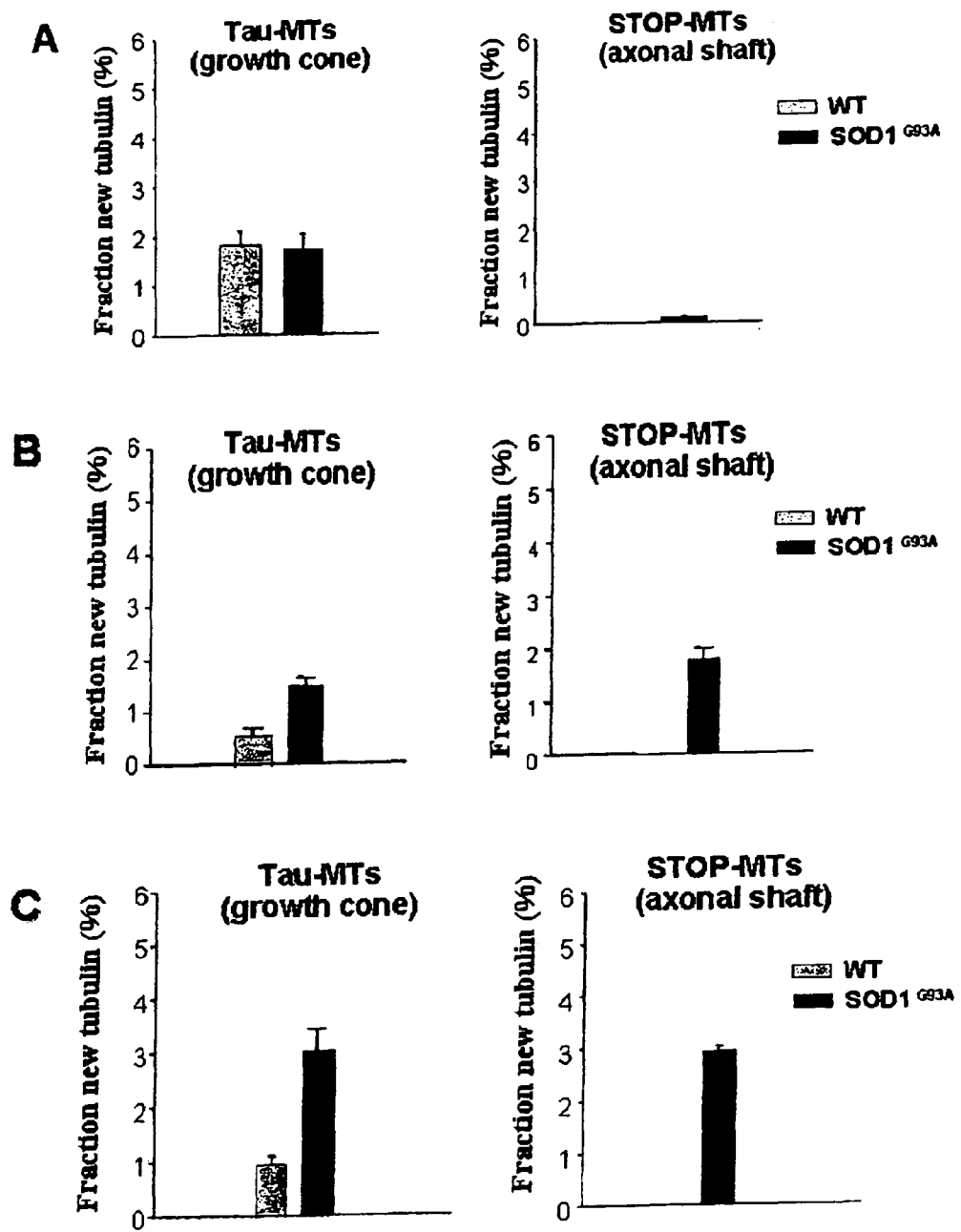
FIG. 4. Measurement of microtubule dynamics during the course of progressive axonal dysfunction in SOD-G93A TGN mice. Wild type and SOD1-G93A TGN mice (n=3 per group) were labeled at 7 weeks (A), 8.5 weeks (B) and 12.5 weeks of age (C) with $^2H_2O$, respectively. Sciatic nerve was dissected, and purified distinct microtubule populations (growth cone and axonal shaft) were hydrolyzed. H incorporation into C—H bonds of alanine was measured by NCI-GC/MS and expressed as fractional synthesis (% newly synthesized during the labeling period; mean±SD). Animals were labeled with $^2H_2O$ for 48 hours (ca. 5% body water enrichment).
Figure 5:
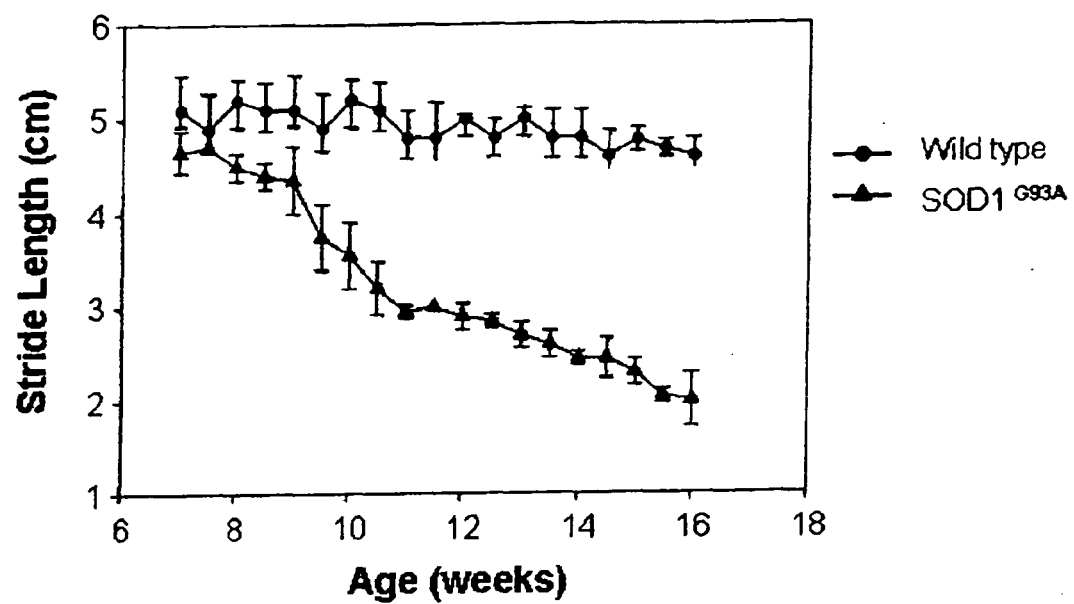
FIG. 5. Quantitative analysis of walking footprint patterns produced by wild-type and SOD1-G93A TGN mice based on measurements of stride length. At 7 weeks of age the stride length measurement of SOD1-G93A TGN mice are indistinguishable from those produced by wild type mice, but by 8.0 weeks of age, SOD1-G93A TGN mice start to exhibit reduced stride length, as compared with the wild type control mice. Graph shows mean±SD for n=3 mice for each group at each age and each measure.

In normal mice, structural microtubules in the sciatic nerve exhibit extremely low rates of assembly and disassembly, or turnover, from tubulin dimers (see FIGS. 1 and 3). In contrast, SOD mice exhibit extreme instability or dynamicity of the same structural microtubules in the sciatic nerve (see FIG. 4). Importantly, this loss of stability of structural microtubules in sciatic nerves is present before behavioral signs or symptoms are observable in these animals, confirming a primary rather than a secondary role in disease pathogenesis. The axonal dysfunction of ALS which precedes and subsequently results in the later loss of axonal transport in motoneurons of SOD mice, therefore, appears to be due to a failure of control processes that normally keep axonal microtubule polymers stable in these neurons.

Thus, drugs that modulate microtubules by regulating their rate of assembly and disassembly (i.e., their "dynamicity") might treat the core pathogenesis of ALS and other motoneuron diseases. Microtubule modulating agents are known, but they have never been recognized as having potential therapeutic use in motoneuron diseases such as ALS, Parkinson's disease, and diabetic neuropathy. Applicants' identification of the kinetic basis of axonal dysfunction in the SOD transgenic mouse model of ALS endowed potential modulators of microtubule dynamicity with a potentially new therapeutic role.

The results of subsequent administration to living animals of drugs known to interact with the microtubule system, alone or in combination with drugs that act on other neuronal receptors, pathways, or systems, confirmed the discovery that microtubule dynamicity represents a new and fundamental therapeutic target in motoneuron disease. In particular, the administration of the noscapine-MK801 combination to SOD1$^{G93A}$ TGN mice not only delayed the onset of disease symptoms and prolonged the duration of survival (see FIG. 6), but reduced neuronal microtubule dynamicity toward normal (see FIG. 7). The correlation between partial normalization of the abnormal microtubule dynamicity (a biochemical metric) and partial amelioration of clinical disease (functional neurologic outcome) supports an etiologic link between microtubule dynamics and motoneuron disease and also suggests room for further therapeutic improvement (i.e., if agents that fully normalize altered microtubule dynamics can be identified).

Use of the assay of microtubule dynamics in the sciatic nerve of SOD transgenic mice as outlined herein as a biomarker of drug activity also allows rapid optimization of new classes of therapy for motoneuron diseases including ALS, Parkinson's disease, and diabetic neuropathy. By using either general screens, or screens of particular classes of drugs, optimal dosages, compounds, regimens etc., can be rapidly tested (e.g., within a few days or weeks) in presymptomatic SOD transgenic mice, rather than having to wait for symptom scores or death.

The invention further provides a method for assaying microtubule dynamics in patients with neuropathies or motoneuron diseases, such as ALS, Parkinson's disease, and diabetic neuropathy. Phase I/II clinical trials can, in principle, include sciatic nerve biopsies for quantification of microtubule dynamics. Thus, the availability of an authentic biomarker for a motoneuron disease such as ALS—i.e., a measurable biochemical abnormality shared by patients with ALS and playing an etiologic role in the disease, thereby representing a target for drug intervention and a metric of drug efficacy—provides several unique advantages for testing classes of ALS (and other motoneuron diseases) drugs. Ineffective agents are identified rapidly, to avoid wasting valuable clinical trial time, money and patient resources. Dose-optimization, patient stratification and subgroup analysis are among the other utilities that a kinetic biomarker provides in motoneuron disease clinical trials.

Administering Isotope-Labeled Precursor(s)

As a first step in the method of the invention, isotope-labeled precursors are administered to living systems. "Living system" includes, but is not limited to, cells, cell lines, animal models of disease, guinea pigs, rabbits, dogs, cats, other pet animals, mice, rats, nonhuman primates, and humans. An "individual" is a vertebrate, usually a mammal, particularly a human, and by "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In general, a "test subject" as used herein is an individual who is being evaluated for changes in spinal cord motoneuron microtubule dynamics and/or for alterations in motoneuron disease symptoms.

While a variety of biological samples can be taken in test living systems, in general, motoneuron samples are used herein. Examples of motoneuron samples include, but are not limited to, sciatic or peripheral nerve tissue and samples from the motor cortex of the brain.

The first step in measuring molecular flux rates involves administering an isotope-labeled precursor molecule to a living system. Modes of administering isotope-labeled precursor molecules may vary, depending upon the absorptive properties of the isotope-labeled precursor molecule and the specific biosynthetic pool into which each compound is targeted. Precursors may be administered to organisms, including experimental animals and humans directly for in vivo analysis.

Generally, an appropriate mode of administration is one that produces a steady state level of precursor within the biosynthetic pool and/or in a reservoir supplying such a pool for at least a transient period of time. Intravascular or oral routes of administration are commonly used to administer such precursors to organisms, including humans. Other routes of administration, such as subcutaneous or intramuscular administration, optionally when used in conjunction with slow release precursor compositions, are also appropriate. Compositions for injection are generally prepared in sterile pharmaceutical excipients. The selection of which route to administer an isotope-labeled precursor molecules is within the skill of the art.

The isotope-labeled precursor molecule may be a stable isotope or radioisotope. Isotope labels that can be used include, but are not limited to, $^2H$, $^{13}C$, $^{15}N$, $^{18}O$, $^3H$, $^{14}C$, $^{35}S$, $^{32}P$, $^{125}I$, $^{131}I$, or other isotopes of elements present in organic systems.

In one embodiment, the isotope label is $^2H$.

The precursor molecule may be any molecule having an isotope label that is incorporated into the "monomer" or "subunit" of interest, or it can be the monomer itself. Isotope labels may be used to modify all precursor molecules disclosed herein to form isotope-labeled precursor molecules. "Isotope labeled substrate" includes any isotope-labeled precursor molecule that is able to be incorporated into a molecule of interest in a living system. Examples of isotope labeled substrates include, but are not limited to, $^2H_2O$, $^3H_2O$, $^2H$-glucose, $^2H$-labeled amino acids, $^2H$-labeled organic molecules, $^{13}C$-labeled organic molecules, $^{14}C$-labeled organic molecules, $^{13}CO_2$, $^{14}CO_2$, $^{15}N$-labeled organic molecules and $^{15}NH_3$.

The entire precursor molecule may be incorporated into one or more tubulin dimer subunits. Alternatively, a portion of the precursor molecule may be incorporated into the tubulin dimer subunits.

A protein precursor molecule may be any protein precursor molecule known in the art. These precursor molecules include, but are not limited to, $CO_2$, $NH_3$, glucose, lactate, $H_2O$, acetate, and fatty acids.

Precursor molecules of proteins may also include one or more amino acids. The precursor may be any amino acid. The precursor molecule may be a singly or multiply deuterated amino acid. For example, the precursor molecule may be one or more $^{13}C$-lysine, $^{15}N$-histidine, $^{13}C$-serine, $^{13}C$-glycine, $^2H$-leucine, $^{15}N$-glycine, $^{13}C$-leucine, $^2H_5$-histidine, and any deuterated amino acid. Labeled amino acids may be administered, for example, undiluted or diluted with non-labeled amino acids. All isotope-labeled precursors may be purchased commercially, for example, from Cambridge Isotope Labs (Andover, Mass.).

Protein precursor molecules may also include any precursor for post-translationally or pre-translationally modified amino acids. These precursors include but are not limited to precursors of methylation such as glycine, serine or $H_2O$; precursors of hydroxylation, such as $H_2O$ or $O_2$; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; precursors of glycosylation and other post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^2H_2O$ in body water may be identified. The total number of C—H bonds in each non essential amino acid is known—e.g., 4 in alanine, 2 in glycine, etc.

The precursor molecule for proteins may be water (e.g., heavy water). The hydrogen atoms on C—H bonds are the hydrogen atoms on amino acids that are useful for measuring protein synthesis from $^2H_2O$ since the O—H and N—H bonds of proteins are labile in aqueous solution. As such, the exchange of 2H-label from $^2H_2O$ into O—H or N—H bonds occurs without the synthesis of proteins from free amino acids. C—H bonds undergo incorporation from $H_2O$ into free amino acids during specific enzyme-catalyzed intermediary metabolic reactions. The presence of 2H-label in C—H bonds of protein-bound amino acids after $^2H_2O$ administration therefore means that the protein was assembled from amino acids that were in the free form during the period of $2H_2O$ exposure—e.g., that the protein is newly synthesized. Analytically, the amino acid derivative used must contain all the C—H bonds but must remove all potentially contaminating N—H and O—H bonds.

Hydrogen atoms (e.g., deuterium or tritium) from body water may be incorporated into free amino acids. $^2H$ or $^3H$ from labeled water can enter into free amino acids in the cell through the reactions of intermediary metabolism, but $^2H$ or $^3H$ cannot enter into amino acids that are present in peptide bonds or that are bound to transfer RNA. Free essential amino acids may incorporate a single hydrogen atom from body water into the α-carbon C—H bond, through rapidly reversible transamination reactions. Free non-essential amino acids contain a larger number of metabolically exchangeable C—H bonds, of course, and are therefore expected to exhibit higher isotopic enrichment values per molecule from $^2H_2O$ in newly synthesized proteins.

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histidine, the hydroxyl group in hydroxyproline or hydroxylysine, and others. Other amino acid synthesis pathways are known to those of skill in the art.

Oxygen atoms ($H_2^{18}O$) may also be incorporated into amino acids from $^{18}O_2$ through enzyme-catalyzed reactions (including hydroxyproline, hydroxylysine or other post-translationally modified amino acids). For example, oxygen exchange into the carboxylic acid moiety of amino acids may occur during enzyme-catalyzed reactions. Incorporation of labeled oxygen into amino acids is known to one of skill in the art.

Hydrogen and oxygen labels from labeled water also may be incorporated into amino acids through post-translational modifications. In one embodiment, the post-translational modification already may include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange-labeled hydrogens from body water, either before or after post-translational modification step (e.g., methylation, hydroxylation, phosphorylation, prenylation, sulfation, carboxylation, acetylation, glycosylation, or other known post-translational modifications).

Protein precursors that are suitable for administration into a subject include, but are not limited to, $H_2O$, $CO_2$, $NH_3$ and $HCO_3$, in addition to the standard amino acids found in proteins as described, supra.

Water is a precursor of proteins as well as other biological molecules (see U.S. patent application Ser. No. 10/279,399, hereby incorporated by reference in its entirety). As such, labeled water may serve as a precursor in the methods taught herein. "Isotope-labeled water" includes water labeled with one or more specific heavy isotopes of either hydrogen or oxygen. Specific examples of isotope-labeled water include $^2H_2O$, $^3H_2O$, and $H_2^{18}O$.

$H_2O$ availability is probably never limiting for biosynthetic reactions in a cell (because $H_2O$ represents close to 70% of the content of cells, or >35 molar concentration), but hydrogen and oxygen atoms from $H_2O$ contribute stoichiometrically to many reactions involved in biosynthetic pathways: e.g.: R—CO—CH2-COOH+NADPH+$H_2O$→R—CH2CH2COOH (fatty acid synthesis).

As a consequence, isotope labels provided in the form of H- or O-isotope-labeled water is incorporated into biological molecules as part of synthetic pathways. Hydrogen incorporation can occur in two ways: into labile positions in a molecule (i.e., rapidly exchangeable, not requiring enzyme catalyzed reactions) or into stable positions (i.e., not rapidly exchangeable, requiring enzyme catalysis). Oxygen incorporation occurs in stable positions.

Some of the hydrogen-incorporating steps from cellular water into C—H bonds in biological molecules only occur during well-defined enzyme-catalyzed steps in the biosynthetic reaction sequence, and are not labile (exchangeable with solvent water in the tissue) once present in the mature end-product molecules. For example, the C—H bonds on glucose are not exchangeable in solution. In contrast, each of the following C—H positions exchanges with body water during reversal of specific enzymatic reactions: C-1 and C-6, in the oxaloacetate/succinate sequence in the Krebs' cycle and in the lactate/pyruvate reaction; C-2, in the glucose-6-phosphate/fructose-6-phosphate reaction; C-3 and C-4, in the glyceraldehyde-3-phosphate/dihydroxyacetone-phosphate reaction; C-5, in the 3-phosphoglycerate/glyceraldehyde-3-phosphate and glucose-6-phosphate/fructose-6-phosphate reactions.

Labeled hydrogen or oxygen atoms from water that are covalently incorporated into specific non-labile positions of a molecule thereby reveals the molecule's "biosynthetic history"—i.e., label incorporation signifies that the molecule was synthesized during the period that isotope-labeled water was present in cellular water.

The labile hydrogens (non-covalently associated or present in exchangeable covalent bonds) in these biological molecules do not reveal the molecule's biosynthetic history. Labile hydrogen atoms can be easily removed by incubation with unlabelled water ($H_2O$) (i.e., by reversal of the same non-enzymatic exchange reactions through which $^2H$ or $^3H$ was incorporated in the first place), however:

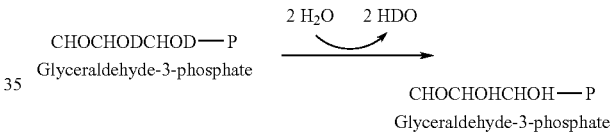

CHOCHODCHOD—P
Glyceraldehyde-3-phosphate

CHOCHOHCHOH—P
Glyceraldehyde-3-phosphate

As a consequence, potentially contaminating hydrogen label that does not reflect biosynthetic history, but is incorporated via non-synthetic exchange reactions, can easily be removed in practice by incubation with natural abundance $H_2O$.

Figure 2:
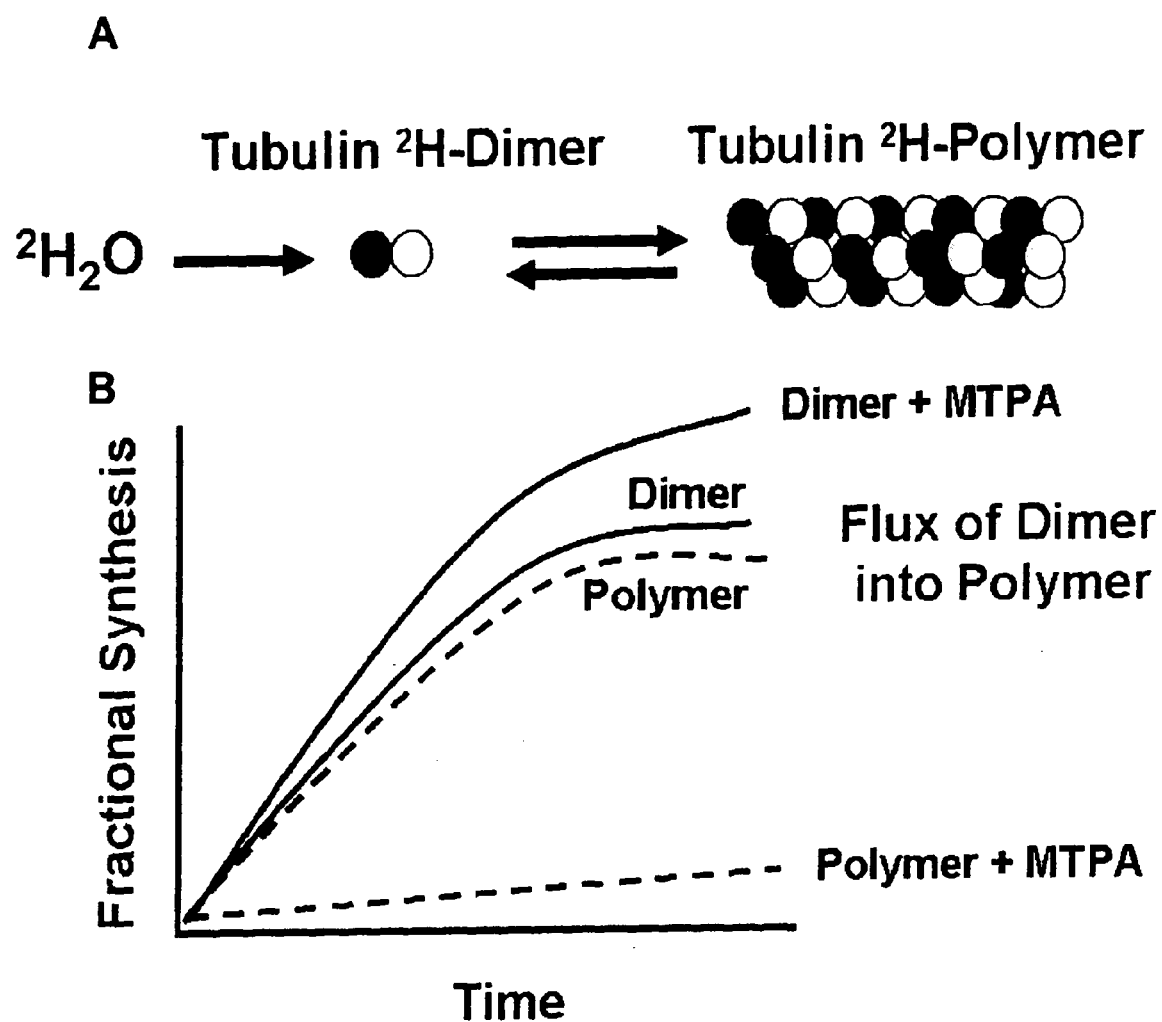
FIG. 2 shows the incorporation of 2H-labeled tubulin dimers into microtubule polymers.

FIG. 1 depicts pathways of labeled hydrogen ($^2H$ or $^3H$) exchange from isotope-labeled water into selected free amino acids which are then incorporated into tubulin dimers, the subunits of microtubules. FIG. 2 shows the incorporation of tubulin dimers into microtubules. FIG. 3 depicts the experimental strategy of isolating and measuring neuronal microtubule populations.

Analytic methods are available for measuring quantitatively the incorporation of labeled hydrogen atoms into biological molecules (e.g., liquid scintillation counting for $^3H$; mass spectrometry, laser spectroscopy, NMR spectroscopy or other methods known in the art for $^2H$ and $^{18}O$). For further discussions on the theory of isotope-labeled water incorporation, see, for example, Jungas R L. *Biochemistry*. 1968 7:3708-17, incorporated herein by reference.

Labeled water may be readily obtained commercially. For example, $^2H_2O$ may be purchased from Cambridge Isotope Labs (Andover, Mass.), and $^3H_2O$ may be purchased, e.g., from New England Nuclear, Inc. "Dueterated water" refers to water incorporating one or more $^2H$ isotopes. In general, $^2H_2O$ is non-radioactive and thus, presents fewer toxicity concerns than radioactive $^3H_2O$. $^2H_2O$ may be administered, for example, as a percent of total body water, e.g., 1% of total body water consumed (e.g., for 3 liters water consumed per day, 30 microliters $^2H_2O$ is consumed). If $^3H_2O$ is utilized, then a non-toxic amount, which is readily determined by those of skill in the art, is administered.

Relatively high body water enrichments of $^2H_2O$ (e.g., 1-10% of the total body water is labeled) may be achieved relatively inexpensively using the techniques of the invention. This water enrichment is relatively constant and stable as these levels are maintained for weeks or months in humans and in experimental animals without any evidence of toxicity. This finding in a large number of human subjects (>100 persons) is contrary to previous concerns about vestibular toxicities at high doses of $^2H_2O$. One of the Applicants has discovered that as long as rapid changes in body water enrichment are prevented (e.g., by initial administration in small, divided doses), high body water enrichments of $^2H_2O$ can be maintained with no toxicities. For example, the low expense of commercially available $2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool, than for 12 hours labeling of $^2H$-leucine at 10% free leucine enrichment, and thus 7-8% enrichment in leucine precursor pool for that period).

Relatively high and relatively constant body water enrichments for administration of $H_2^{18}O$ may also be accomplished, since the $^{18}O$ isotope is not toxic, and does not present a significant health risk as a result.

Isotope-labeled water may be administered via continuous isotope-labeled water administration, discontinuous isotope-labeled water administration, or after single or multiple administration of isotope-labeled water administration. In continuous isotope-labeled water administration, isotope-labeled water is administered to an individual for a period of time sufficient to maintain relatively constant water enrichments over time in the individual. For continuous methods, labeled water is optimally administered for a period of sufficient duration to achieve a steady state concentration (e.g., 3-8 weeks in humans, 1-2 weeks in rodents).

In discontinuous isotope-labeled water administration, an amount of isotope-labeled water is measured and then administered, one or more times, and then the exposure to isotope-labeled water is discontinued and wash-out of isotope-labeled water from body water pool is allowed to occur. The time course of delabeling may then be monitored. Water is optimally administered for a period of sufficient duration to achieve detectable levels in biological molecules.

Isotope-labeled water may be administered to an individual or tissue in various ways known in the art. For example, isotope-labeled water may be administered orally, parenterally, subcutaneously, intravascularly (e.g., intravenously, intra-arterially), or intraperitoneally. Several commercial sources of $^2H_2O$ and $H_2^{18}O$ are available, including Isotec, Inc. (Miamisburg Ohio, and Cambridge Isotopes, Inc. (Andover, Mass.)). The isotopic content of isotope labeled water that is administered can range from about 0.001% to about 20% and depends upon the analytic sensitivity of the instrument used to measure the isotopic content of the biological molecules. In one embodiment, 4% $^2H_2O$ in drinking water is orally administered. In another embodiment, a human is administered 50 mL of $^2H_2O$ orally.

The individual being administered labeled water may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

Obtaining One or More Targeted Tubulin or Microtubule Polymer Molecules of Interest In practicing the method of the invention, in one aspect, proteins are obtained from a living system according to methods known in the art. In general, samples include motoneurons, which can be obtained from a variety of places in the test subject (e.g., motor-cortex in the brain, sciatic nerve, peripheral nerves), with the sciatic nerve being especially useful.

A plurality of microtubule polymers and/or free tubulin dimer subunits is obtained from the living system using techniques well known in the art of neurobiology. The one or more biological samples may be one or more biological fluids or tissues such as nerve tissue. Proteins may be obtained from a specific group of cells, such as neurons, or other growing or non-growing cells. Proteins also may be obtained, and optionally partially purified or isolated, from the biological sample using standard biochemical methods known in the art. In particular, different microtubule fractions (tau-MTs, STOP-MTs, etc.) are isolated as outlined in PCT/US2005/028069.

The frequency of biological sampling can vary depending on different factors. Such factors include, but are not limited to, ease and safety of sampling, synthesis and breakdown/removal rates of the proteins, and the half-life of a therapeutic candidate agent administered to a cell, animal, or human.

Proteins may be partially purified and/or isolated from one or more biological samples, depending on the assay requirements. In general, microtubule polymers and/or tubulin dimer subunits may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, fast performance liquid chromatography (FPLC), chemical extraction, thin layer chromatography, gas chromatography, and chromatofocusing. For example, some proteins may be purified using a standard antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the assay and components of the system. In some instances no purification will be necessary.

In another embodiment, the proteins may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase degradation). Hydrolysis or degradation may be conducted either before or after purification and/or isolation of the proteins. The proteins also may be partially purified, or optionally, isolated, by conventional purification methods including HPLC, FPLC, gas chromatography, gel electrophoresis, and/or any other methods of separating chemical and/or biochemical compounds known to those skilled in the art.

Analysis

Isotopic enrichment in proteins can be determined by various methods known in the art such as NMR, laser spectroscopy, liquid scintillation counting, Geiger counter, and mass spectrometry. For methods using mass spectrometry, there are several different types of mass spectrometers finding use in the present invention including but not limited to, gas chromatography-mass spectrometry (GC-MS), isotope-ratio mass spectrometry, GC-isotope ratio-combustion-MS, GC-isotope ratio-pyrrolysis-MS, liquid chromatography-MS, electrospray ionization-MS, matrix assisted laser desorption-time of flight-MS, Fourier-transform-ion-cyclotron-resonance-MS, and cycloidal-MS.

Mass spectrometers convert molecules such as proteins into rapidly moving gaseous ions and separate them on the basis of their mass-to-charge ratios. The distributions of isotopes or isotopologues of ions, or ion fragments, may thus be used to measure the isotopic enrichment in a plurality of proteins.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a protein and then generate secondary fragments of the initial ions.

Different ionization methods are also known in the art. One key advance has been the development of techniques for ionization of large, non-volatile macromolecules including proteins. Techniques of this type have included electrospray ionization (ESI) and matrix assisted laser desorption. These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

In general, in order to determine a baseline mass isotopomer frequency distribution for the protein, such a sample is taken before infusion of an isotopically labeled precursor. Such a measurement is one means of establishing in the cell, tissue or organism, the naturally occurring frequency of mass isotopomers of the protein. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of $^{13}C$ present in organic carbon is 1.11%. Methods of determining such isotopomer frequency distributions are discussed below. Typically, samples of the protein are taken prior to and following administration of an isotopically labeled precursor.

In one embodiment, the relative and absolute mass isotopomer abundances are measured. Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the present invention.

In one embodiment, the labeled:unlabeled proportion of proteins such as microtubule polymers is calculated. The proportion of labeled and unlabeled molecules of interest (e.g., tubulin dimers, microtubule polymers) is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686, 5,910,403, and 6,010,846, which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety.

In addition to the above-cited references, calculation software implementing the method is publicly available from Professor Marc Hellerstein, University of California, Berkeley.

The comparison of excess molar ratios to the theoretical patterns can be carried out using a table generated for a molecule of interest, or graphically, using determined relationships. From these comparisons, a value, such as the value p, is determined, which describes the probability of mass isotopic enrichment of a subunit in a precursor subunit pool. This enrichment is then used to determine a value, such as the value $A_{X}^{*}$, which describes the enrichment of newly synthesized proteins for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M_X$, $$\text{Fractional abundance of } M_X = A_X = \frac{\text{Abundance } M_x}{\sum_{i=0}^{n} \text{Abundance } M_i},$$

where 0 to n is the range of nominal masses relative to the lowest mass ($M_0$) mass isotopomer in which abundances occur.

$$\Delta \text{ Fractional abundance (enrichment or depletion)} =$$

$$(A_x)_e - (A_x)_b = \left( \frac{\text{Abundance } M_x}{\sum_{i=0}^{n} \text{Abundance } M_i} \right)_e - \left( \frac{\text{Abundance } M_x}{\sum_{i=0}^{n} \text{Abundance } M_i} \right)_b,$$

where subscript e refers to enriched and b refers to baseline or natural abundance.

In order to determine the fraction of polymers that were actually newly synthesized during a period of precursor administration, the measured excess molar ratio ($EM_x$) is compared to the calculated enrichment value, $A_x^*$, which describes the enrichment of newly synthesized biopolymers (e.g., a microtubule) for each mass isotopomer, to reveal the isotopomer excess ratio which would be expected to be present, if all isotopomers were newly synthesized.

In one embodiment, molecular flux rates are calculated. The method of determining the polymerization and/or depolymerization rate of microtubules includes calculating the proportion of mass isotopically-labeled subunit of a microtubule in the precursor pool, and using this proportion to calculate an expected frequency of a microtubule containing at least one mass isotopically-labeled subunit of a microtubule. This expected frequency is then compared to the actual, experimentally determined isotopomer frequency. From these values, the proportion of microtubule which is formed from added isotopically-labeled precursors during a selected incorporation period can be determined. Thus, the rate of synthesis during such a time period is also determined. In a system at steady-state concentrations, or when any change in concentrations in the system are measurable or otherwise known during said time period, the rate of disassembly is thereby known as well, using calculations known in the art. A precursor-product relationship is then applied. For the continuous labeling method, the isotopic enrichment is compared to asymptotic (e.g., maximal possible) enrichment and kinetic parameters (e.g., synthesis rates) are calculated from precursor-product equations. The fractional synthesis rate (ks) may be determined by applying the continuous labeling, precursor-product formula:

$$k_s = [-\ln(1-f)]/t,$$

where f=fractional synthesis=product enrichment/asymptotic precursor/enrichment
and t=time of label administration of contacting in the system studied.

For the discontinuous labeling method, the rate of decline in isotope enrichment is calculated and the kinetic parameters of subunits are calculated from exponential decay equations. In practicing the method, microtubules are enriched in mass isotopomers, usually containing multiple mass isotopically labeled subunits of microtubules. These higher mass isotopomers of the microtubule (e.g., proteins containing 3 or 4 mass isotopically labeled tubulin dimers) are formed in negligible amounts in the absence of exogenous precursor (e.g., $^2H_2O$), due to the relatively low abundance of natural mass isotopically-labeled precursor (e.g., $^2H_2O$), but are formed in significant amounts during the period of precursor incorporation (e.g., during administration of $^2H_2O$ to the cell, tissue, organ, or organism). The microtubules are taken from the cell, tissue, organ, or organism at the sequential time points and are analyzed by mass spectrometry to determine the relative frequencies of a high mass isotopomer or to determine the relative frequencies of a high mass isotopomer of a subunit from a microtubule. Since the high mass isotopomer is synthesized almost exclusively before the first time point, its decay between the two time points provides a direct measure of the rate of decay of the subunit. The rate of decay of mass isotopomers that do not contain multiple mass isotopically labeled subunits can also be calculated and used by the methods described herein.

Usually, the first time point is at least 2-3 hours after administration of precursor (e.g., $^2H_2O$) has ceased, depending on mode of administration, to ensure that the proportion of mass isotopically labeled subunit (e.g., a labeled tubulin dimer for a microtubule polymer) has decayed substantially from its highest level following precursor administration. In one embodiment, the following time points are typically 1-4 hours after the first time point, but this timing will depend upon the replacement rate of the biopolymer pool.

The rate of decay of the microtubule is determined from the decay curve for the isotope-labeled subunit. In the present case, where the decay curve is defined by several time points, the decay kinetics can be determined by fitting the curve to an exponential decay curve, and from this, determining a decay constant.

Breakdown rate constants (kd) may be calculated based on an exponential or other kinetic decay curve:

$$k_d = [-\ln f]/t.$$

Methods of Screening for Modulators of Motoneuron Diseases

The invention provides methods of screening for modulators of motoneuron diseases (see FIGS. 4-7, 10). "Modulators" in this context means agonists and antagonists of activity, with antagonists being particularly useful. A modulator is selected such that dysfunctional activity is suppressed and any associated carrier side-effects are minimized.

The present invention is directed in part to the discovery that biochemical pathways that effect microtubule dynamics in motoneurons lead to treatments of motoneuron diseases. Accordingly, in one embodiment, the invention provides methods of screening candidate agents to identify those agents that alter axonal microtubule dynamicity, and thus can treat, prevent or ameliorate the symptoms of motoneuron diseases.

In general, there are three classes of candidate agents which find use in the present invention. The first class is comprised of general candidate agents that are evaluated for the ability to modulate microtubule dynamics, and in particular, the ability to differentiate between axonal shaft microtubules and growth cone and/or MAP2 microtubules. That is, as the present invention outlines, these two pools of microtubules exhibit very different tubulin exchange kinetics, with agents that preferentially stabilize axonal microtubules being of particular use. Thus screening of candidate agent libraries is done for agents that alter (e.g., modify) microtubule dynamics and thus motoneuron dysfunction.

Secondly, pathway-specific candidate agents can be tested. In this embodiment, agents suspected or known to affect microtubule exchange kinetics are tested in motoneuron systems as outlined herein.

Additionally, there are a number of biochemical events that are known to be associated with motoneuron diseases but are generally believed to act on neuronal systems other than microtubules. In some cases, these biochemical events are acting at the level of the motoneuron; in others, these events are associated with later stage events that can affect progression of both CNS and peripheral nervous system (PNS) diseases. For example, in later stage Parkinson's disease, motoneuron activity can be disrupted. Similarly, in later stage ALS, microglial activation occurs. Accordingly, combination therapy approaches including those outlined herein can be very useful. Thus, the present invention provides for evaluating agents, and combinations of agents, that are known to be involved in these disease states, using microtubule dynamics as a readout of neuroprotective activity. These additional pathways include the inflammation associated with microglia activation and pathways associated with oxidative stress, as well as others known in the art.

General Candidate Agents

In one embodiment, candidate agents are screened for their ability to modulate microtubule activity in motoneurons. "Candidate agent" or "candidate drug" as used herein describes any molecule, e.g., proteins including biotherapeutics including antibodies and enzymes, small organic molecules including known drugs and drug candidates, polysaccharides, fatty acids, vaccines, nucleic acids, etc. that can be screened for activity as outlined herein. In this context, a "general" candidate agent is one not known to be associated with modulation of microtubules, motoneurons, and/or motoneuron diseases.

Candidate agents encompass numerous chemical classes. In one embodiment, the candidate agent is an organic molecule, usually small organic compounds having a molecular weight of more than 100 and less than about 2,500 daltons. Particularly useful are small organic compounds having a molecular weight of more than 100 and less than about 2,000 daltons, more usefully less than about 1500 daltons, more usefully less than about 1000 daltons, more usefully less than 500 daltons. Candidate agents comprise functional groups necessary for structural interaction with proteins, particularly hydrogen bonding, and typically include at least one of an amine, carbonyl, hydroxyl or carboxyl group, usually at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression and/or synthesis of randomized oligonucleotides and peptides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The candidate bioactive agents may be proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In a particularly useful embodiment, the amino acids are in the (S) or L-configuration. If non-naturally occurring side chains are used, non-amino acid substituents may be used, for example to prevent or retard in vivo degradations.

The candidate bioactive agents may be naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the systems described herein. Useful in this embodiment are libraries of bacterial, fungal, viral, and mammalian proteins, with the latter being particularly useful, and human proteins being especially useful.

The candidate agents may be antibodies, a class of proteins. The term "antibody" includes full-length as well antibody fragments, as are known in the art, including Fab, Fab2, single chain antibodies (Fv for example), chimeric antibodies, humanized and human antibodies, etc., either produced by the modification of whole antibodies or those synthesized de novo using recombinant DNA technologies, and derivatives thereof.

The candidate bioactive agents may be nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook, and peptide nucleic acids. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence, including restriction fragments, viruses, plasmids, chromosomes, etc. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, 4-acetylcytosine, 8-hydroxy-$N^6$-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.etc. It should be noted in the context of the invention that nucleosides (ribose plus base) and nucleotides (ribose, base and at least one phosphate) are used interchangeably herein unless otherwise noted.

As described above generally for proteins, nucleic acid candidate bioactive agents may be naturally occurring nucleic acids, random and/or synthetic nucleic acids. For example, digests of procaryotic or eucaryotic genomes may be used as is outlined above for proteins. In addition, RNAis are included herein.

Screening of Pathway-Based Candidate Agents

As outlined above, in addition to general candidate agents, the invention finds use in screening for modulators of microtubule activity, motoneuron dysfunction and/or motoneuron diseases. By "microtubule activity" herein is meant one of a variety of microtubule biological activities, including, but not limited to, the rate of microtubule polymerization and/or depolymerization, the ability to sustain the transport of cellular components from one cellular location to another, the cytoskeletal function of microtubules, etc.

In general, there are two types of pathway-based candidate agents that are screened; those known or suspected to be involved in microtubule activity, and those that are involved in other biochemical events associated with motoneuron diseases.

Accordingly, some embodiments of the invention utilize screening of pathway-based candidate agents.

Microtubule Target Modulating Agents (MTMAs)

In one embodiment, microtubule target modulating agents are tested. By "microtubule target modulating agent" or "MTMA" herein is meant an agent that has been previously recognized or proposed to affect the rate of microtubule polymerization and/or depolymerization, and in particular to reduce or slow microtubule instability (i.e., dynamicity).

In one embodiment, the MTMAs are opioids and opioid derivatives. There are four broad classes of opioids: endogenous opioid peptides, produced in the body; opium alkaloids, such as morphine (the prototypical opioid) and codeine; semi-synthetic opioids such as heroin and oxycodone; and fully synthetic opioids such as pethidine and methadone that have structures unrelated to the opium alkaloids.

In one embodiment, the MTMAs are opium alkaloids. In one embodiment, the opium alkaloid is noscapine or noscapine derivatives such as outlined in U.S. Pat. No. 6,376,516, hereby incorporated by reference in its entirety. Noscapine is an opium alkaloid that lacks analgesic or anticonvulsant activity, and contrary to other opioids (e.g., morphine) is not a narcotic or an addicting compound. Furthermore, in contrast to other microtubule-interacting agents such as paclitaxel, nocodazole, vinblastine and colchicine, noscapine modifies microtubule dynamics without affecting total tubulin polymer mass and without altering the steady-state dimer/polymer equilibrium of microtubule assembly both in vitro and in living cells. Noscapine penetrates the blood brain barrier and has long half-life in CNS tissue (brain and spinal cord) and PNS too. Therefore, we identified noscapine as a potential microtubule-interactive chemotherapeutic agent for CNS and PNS disorders associated with cytoskeletal abnormalities such as altered microtubule dynamics as we have discovered (see FIGS. 4-7). Noscapine is currently available for human use as a cough suppressant. Other opium alkaloids useful as MTMAs are the phenanthrenes, isoquinolines and papaverine.

In addition, the cannabinoids find use in screening alone or in combination with other agents. Cannabinoids are a group of chemicals which activate the body's endogenous cannabinoid receptors, including CB1 and CB2 receptor. Currently, there are three general types of cannabinoids: herbal cannabinoids occur uniquely in the cannabis plant; endogenous cannabinoids are produced in the bodies of humans and other animals; and synthetic cannabinoids are similar compounds produced in the laboratory. Suitable agents include, but are not limited to: anandamide and analogs of anandamide, docosatetraenylethanolamide and homo-γ linoenylethanolamide; endocannabinoids such as 2-arachidonoylglycerol (2-AG), palmitoyl ethanolamide and oleamide; tetrahydrocannabinol (THC), particularly Marinol ($\Delta^9$-THC), cannabidiol (CDB); cannabinol (CBN); Cannabigerol; Cannabichromene; Cannabicyclol; Cannabivarol; Tetrahydrocannabivarin; Cannabidivarin; Cannabichromevarin; Cannabigerovarin; Cannabigerol Monoethyl Ether, CP-55940; HU-210 100; SR-144526; and Nabilone.

Other pathway-based candidate agents are those that target the intracellular concentration of ions, particularly calcium and sodium. Intracellular concentration of calcium is known to be involved in microtubule formation and stability, and thus agents that modulate intracellular calcium (particularly by decreasing intracellular calcium concentrations) are of particular interest for screening.

Ion Channel Antagonists

There are three main types of ligand-gated ion channels (ionotropic receptors) that are involved in the L-glutamate pathway, a major excitatory neurotransmitter. These are the NMDA, AMPA and kainate receptors, each of which modulators finds use in pathway screening in the present invention.

NMDA Receptor Antagonists

The NMDA receptor was first identified by the selective activation by N-methyl-D-aspartate (NMDA). NMDA receptors are composed of assemblies of NR1 subunits and NR2 subunits, which can be one of four separate gene products (NR2A-D). Expression of both subunits is required to form functional channels. The glutamate binding domain is formed at the junction of NR1 and NR2 subunits (hence the need for both subunits to be expressed). In addition to glutamate, the NMDA receptor requires a co-agonist, glycine, to bind to allow the receptor to function. The glycine binding site is found on the NR1 subunit. The NR2B subunit also possesses a binding site for ployamines, regulatory molecules that modulate the functioning of the NMDA receptor. In addition to the glutamate (NMDA) binding site, there are also multiple binding sites on the NMDA receptor for modulatory compounds. Efficient NMDA receptor activation requires not only NMDA but also glycine. Activation can also be modulated by the binding of polyamines. Each of the binding sites (glutamate, glycine, polyamine) has been used as a potential target for the development of both receptor and sub-type selective compounds.

NMDA inhibitors can be either competitive or non-competitive inhibitors, and can bind to any of the binding sites. Thus, suitable NMDA receptor antagonists include, but are not limited to, Amantadine; ketamine; dextromethorphan (3-methoxy-17-methyl-9(alpha), 13(alpha), 14(alpha)-morphinana hydrobromide monohydrate); Dizocilipine (also known as MK-801); AP-7 (2-amino-7-phosphonoheptanoic acid); APV (also called AP-5; 2-amino-5-phosphonovalerate; DCKA (5,7-dichlorokyneurenic acid; acts at the glycine site), harkoseride (acetamido-N-benzyl-3-methoxypropionate and its metabolite, H-209); homoquinolinic acid, (R)-AP5; (R)-CPP-ene; PBPD; memantine; ketamine; L-701-324; L-689,560; GV196771A; Ro 25-6981; ifenprodil; Co-101676; GW468816 (glycine site antagonist).

Figure 6:
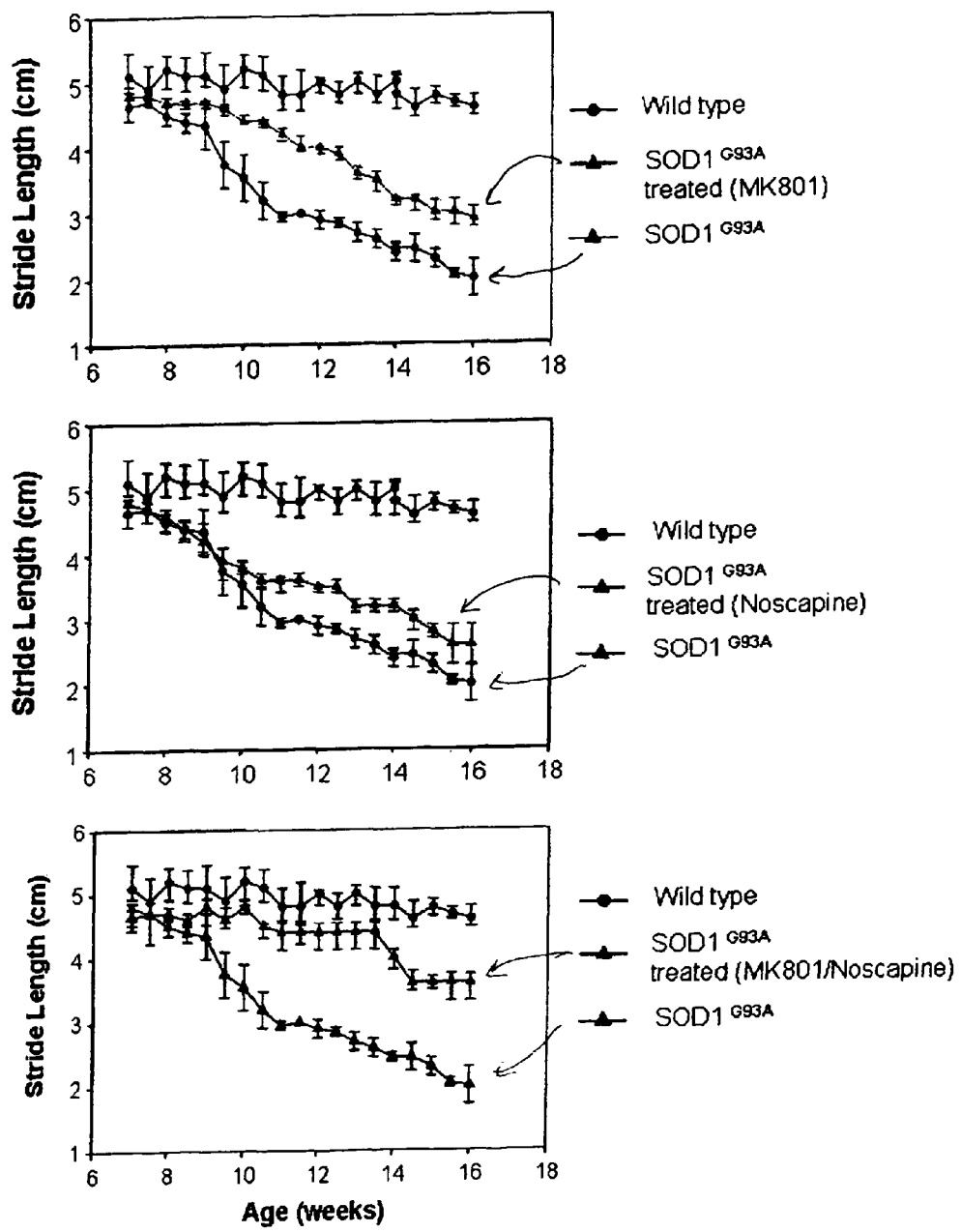
FIG. 6. Noscapine-MK801 combination delays onset of disease and death in SOD1-G93A TGN mice. The one and two-drug treatments were started at an early (i.e., presymptomatic) stage of disease (7 weeks). SOD1-G93A TGN mice were treated 3 times a week with noscapine (0.2 mg/kg body weight) and/or MK-801 (12 mg/kg body weight/day). Mice received noscapine intraperitoneally and MK-801 in drinking water. During stride length measurements, mice treated with the noscapine-MK801 combination performed significantly better than mice treated with either compound alone. The combination of noscapine with MK-801 significantly delayed the onset of symptoms (32 days) and delayed onset of death (by 21 days) as compared with the nontreated SOD1-G93A TGN mice. Graph shows mean±SD for n=3 mice for each group at each age and each measure.
Figure 7:
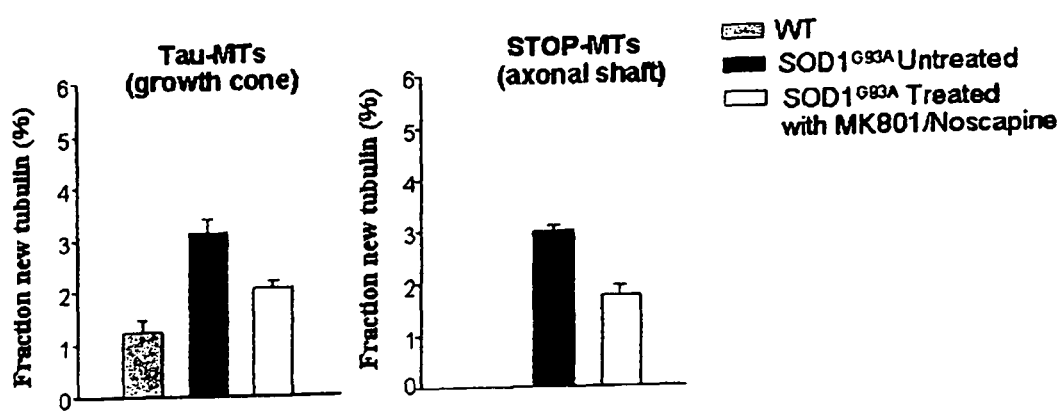
FIG. 7. Effect of Noscapine-MK801 combination on relative dynamics ($^2H$-label incorporation) in microtubule subpopulations in sciatic nerve of 12.5 week old SOD1-G93A TGN mice. Noscapine-MK801 combination in SOD1-G93A TGN mice reduced microtubule dynamics by ~35% in the growth cone and 50% in the axonal shaft as compared with untreated mice. Animals were labeled with $^2H_2O$ for 48 hours. Graph shows mean±SD for n=3 mice for each measure.
Figure 8:
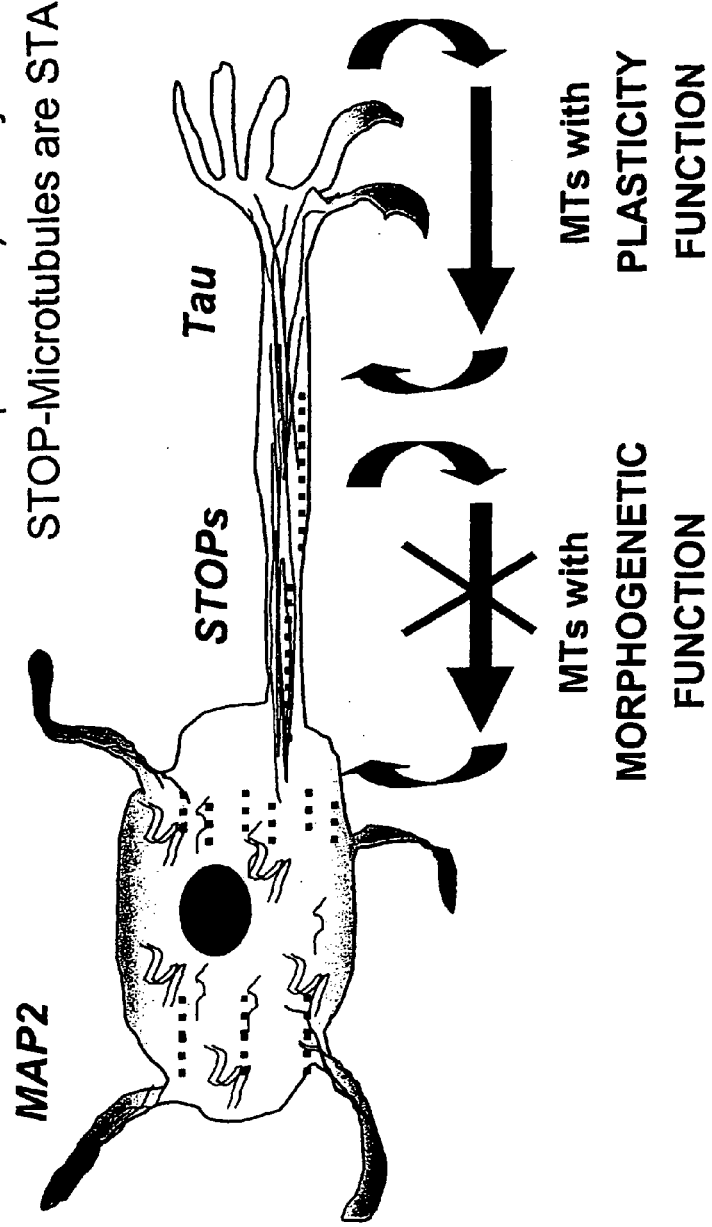
FIG. 8 depicts the specific distribution of microtubule populations within a neuron.
Figure 9:
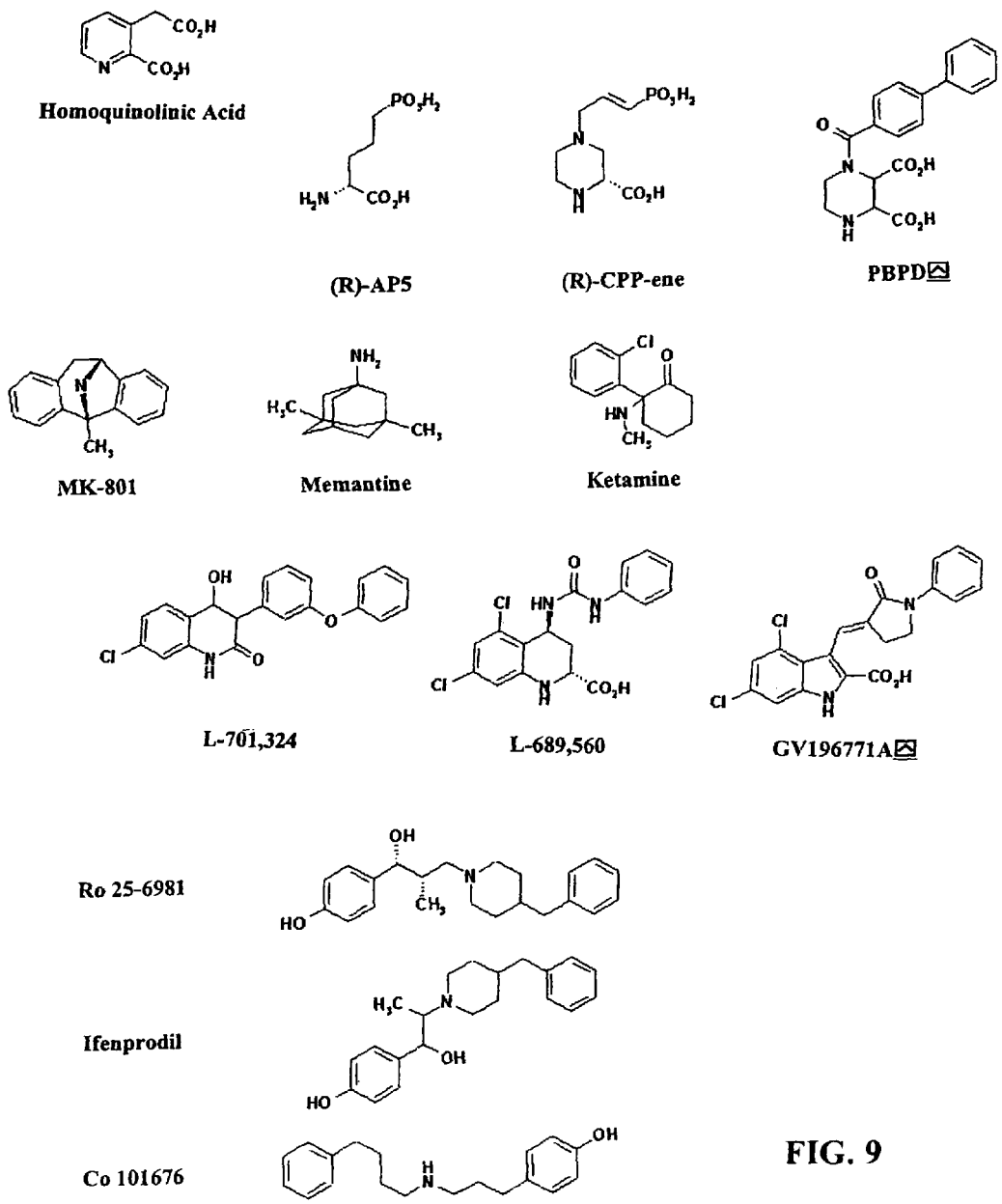
FIG. 9 depicts a number of different NMDA receptor antagonists.
Figure 10:
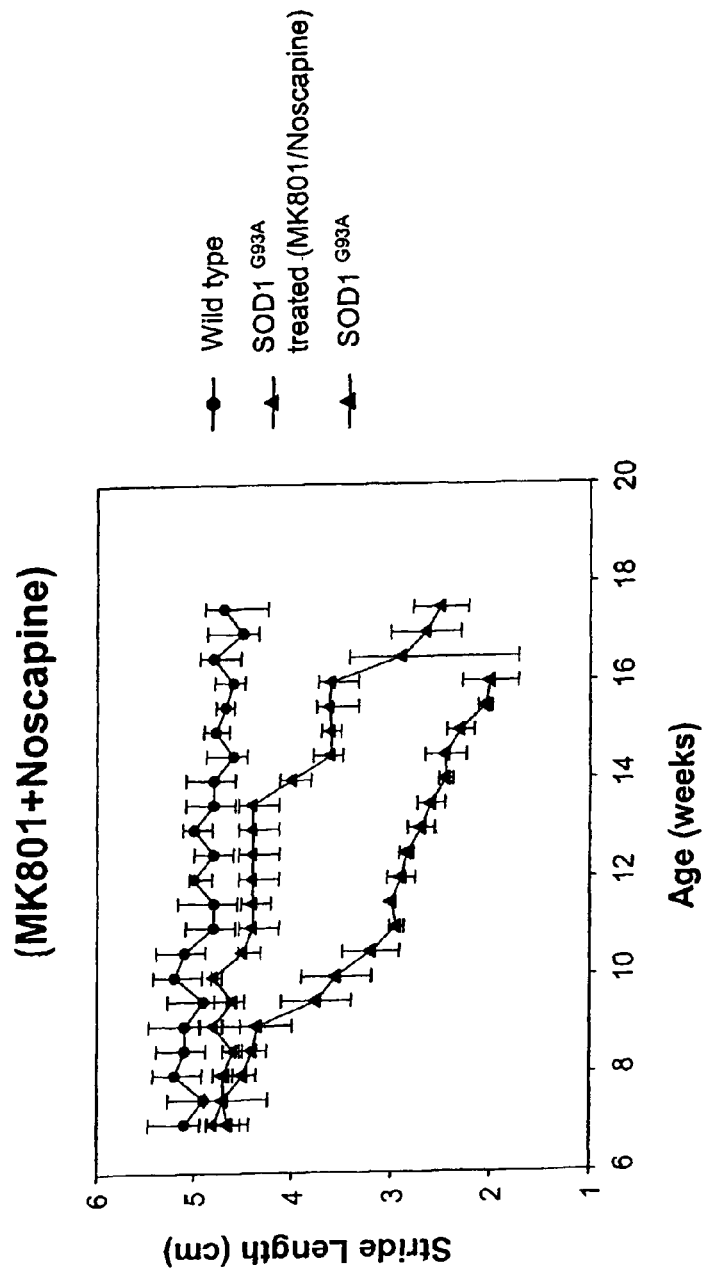
FIG. 10 depicts the 18 week results of administering noscapine-MK801 to the SOD1 mouse model of ALS
Figure 11A:
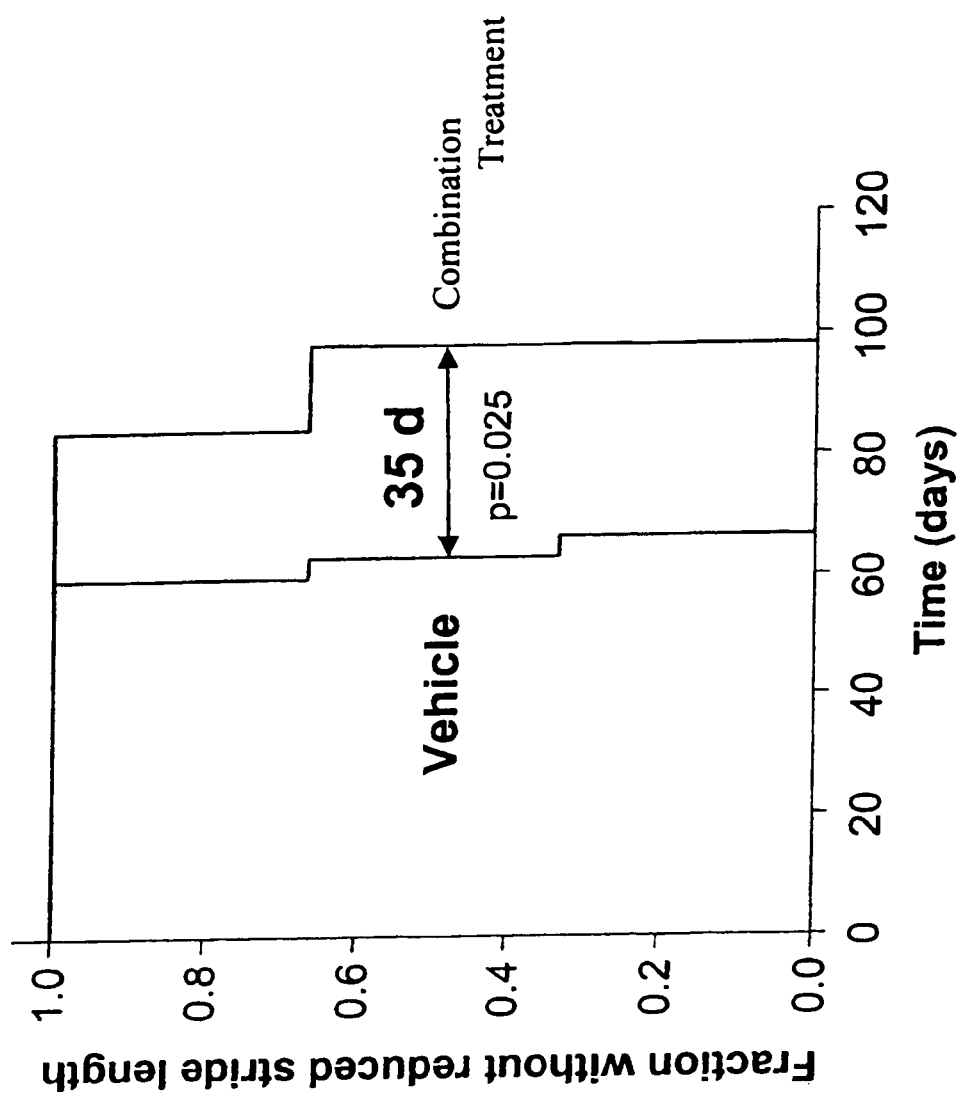
FIGS. 11A, 11B and 11C depict differences in time to first symptoms, time of clinical onset and time to mortality using the invention.
Figure 11B:
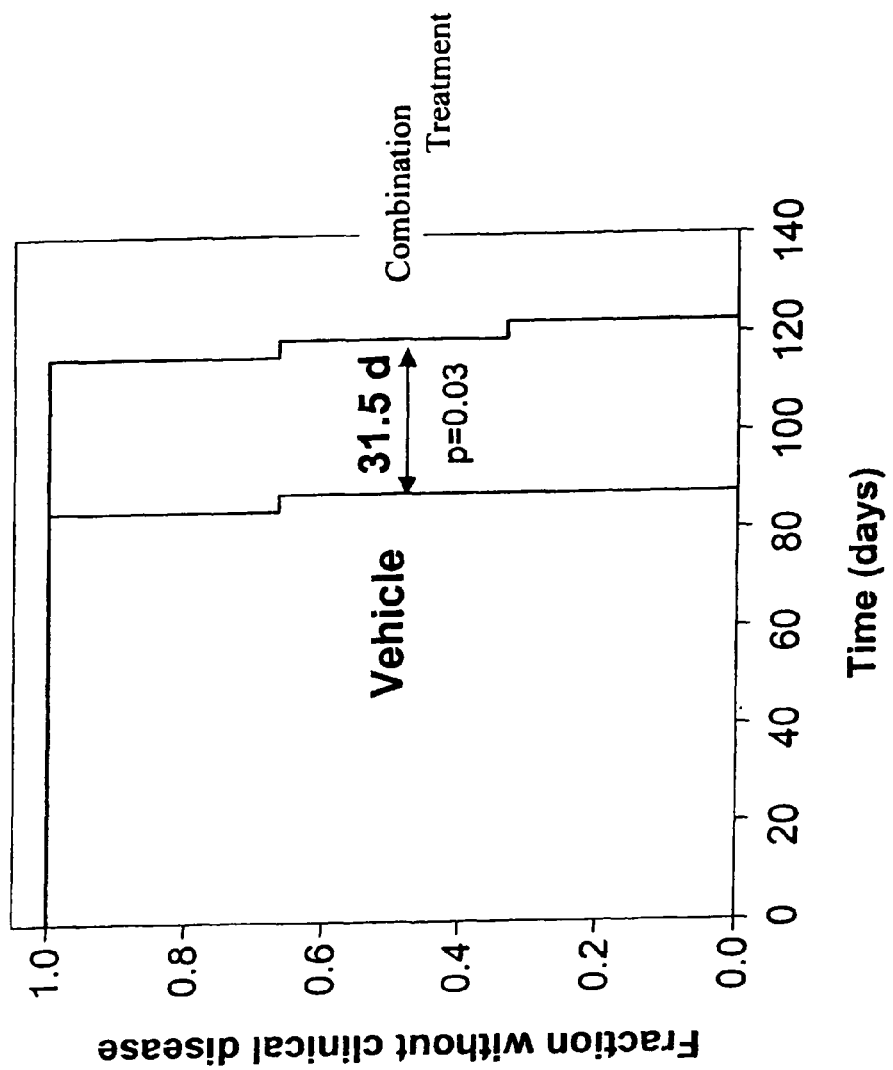
Figure 11C:
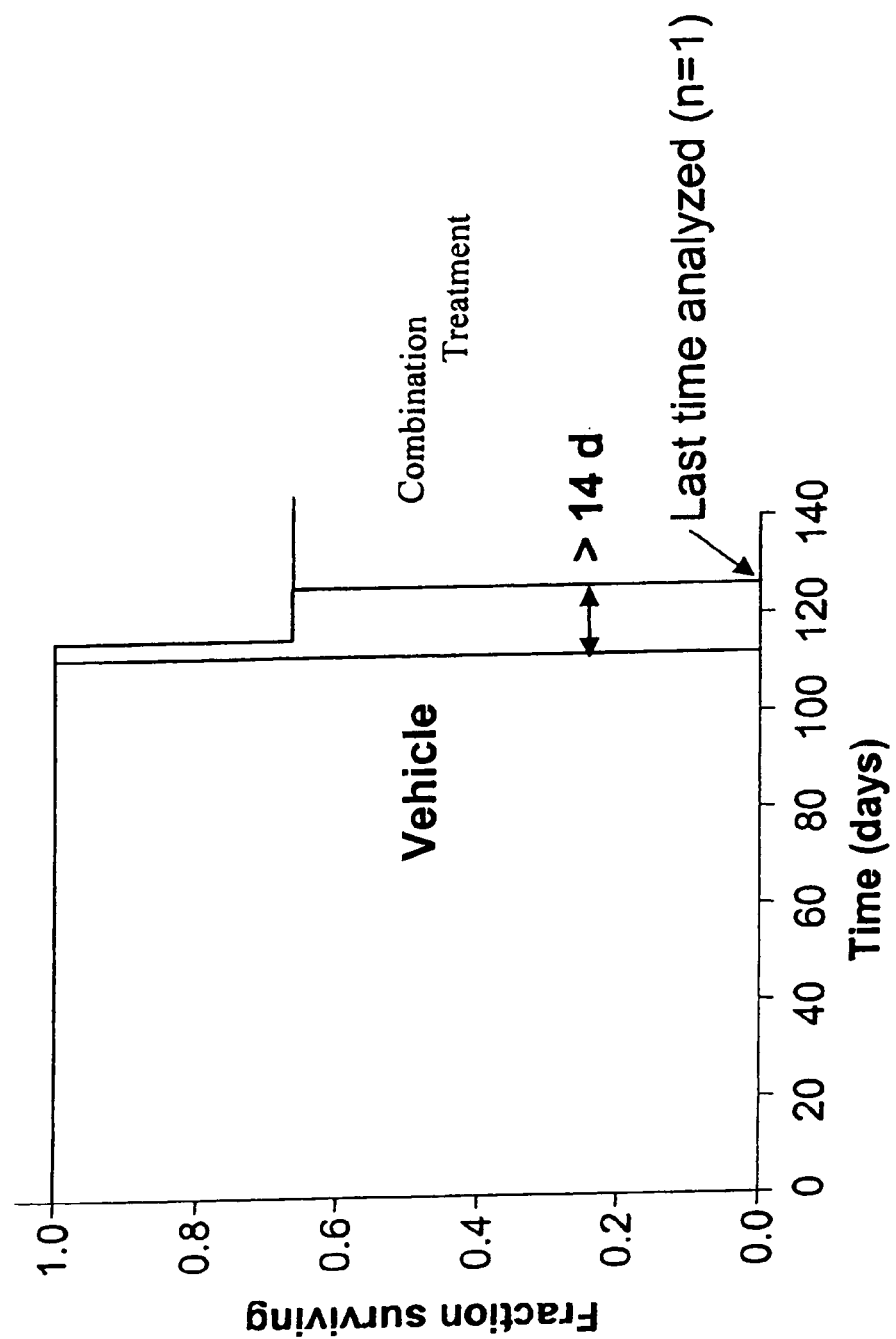
Figure 12:
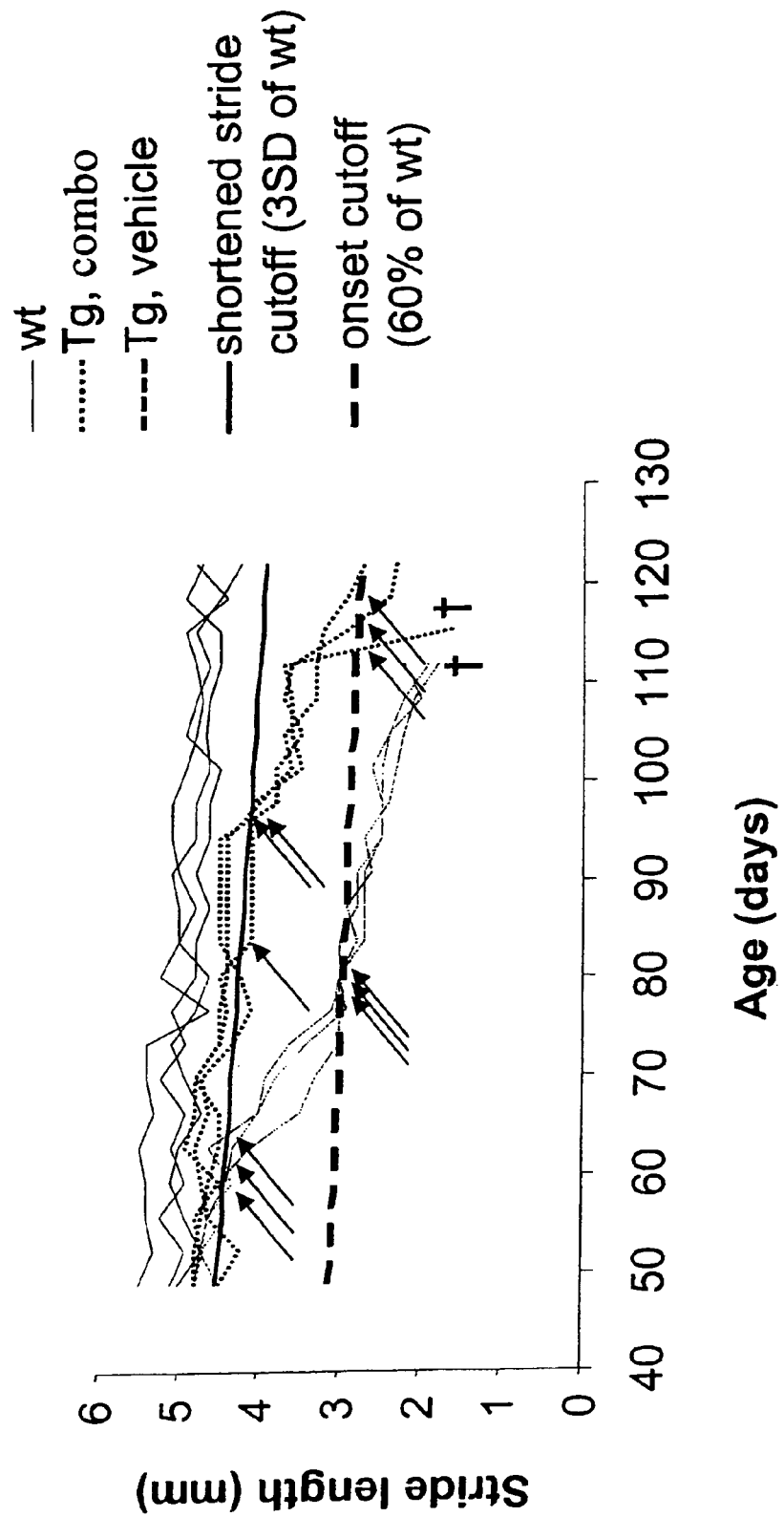
FIG. 12 depicts the overall statistics of survival of different treatments.

Several of these inhibitors are depicted in FIG. 6.

Of particular interest is dizolcipine; dizolcipine has been identified as a calcium channel blocker which decreases the excessive influx of calcium into neurons through the ionic channel NMDA-receptor. It is also classified as a competitive antagonist of the glutamatergic NMDA-receptor subtype and penetrates the blood brain barrier. Glutamate-induced excitotoxicity is complex and multifactorial, but is a major component of the terminal events mediating neuronal injury and death. It involves excessive influx of calcium through the NMDA-receptor.

Modulators of Oxidative Stress

In addition to MTMAs and receptor antagonists, other pathway-selective agents include those that effect oxidative stress in motoneurons. These include general antioxidants such as Vitamin E, procysteine, N-acetylcysteine, lipoic acid, and various types of nitrones.

Microglia Activation

Neuroinflammation has recently emerged as a significant contributor to motoneuron disease. For example, ALS tissue is characterized by inflammatory changes that are observed in both sporadic and familial ALS and in the SOD transgenic mouse model. They include an accumulation of large numbers of activated microglia and astrocytes. Proinflammatory cytokines, such as tumor necrosis factor (TNF), are robustly upregulated in ALS. The receptor for tumor necrosis factor (TNF-R1) is elevated at late presymptomatic as well as symptomatic phases of disease. TNF acts as a principal driver for neuroinflammation in ALS, while several co-stimulating cytokines and chemokines act to potentiate the TNF effects. These changes also are observed for other motoneuron diseases including Parkinson's disease and the various peripheral neuropathies including diabetic neuropathy.

There are several candidate anti-inflammatory drugs that are being tested for efficacy in ALS, including, but not limited to, minocycline and thalidomide.

Thus, the present invention provides for testing of these agents with other candidate agents, particularly microtubule target modulating agents (MTMA), some of which are listed above, ion channel antagonists (some of which also are listed above), antioxidants, copper chelators, inhibitors of nitric oxide and scavenger of peroxynitrite, and neurotrophic factors.

Miscellaneous Agents

In addition, anti-glutamate agents, other anti-inflammatory agents and other anti-convulsants can all be tested. Of course, the invention is not limited by any particular compound in any particular class of compounds. Any compound or any combination of compounds is envisioned for use in the methods of the present invention.

Pharmaceutical Compositions

As outlined herein, there are a variety of pharmaceutical compositions that can be used to treat motoneuron diseases, particularly ALS. In one embodiment, the pharmaceutical composition comprises an MTMA agent and a pharmaceutical carrier, as outlined herein. In this embodiment, noscapine finds particular use.

In many embodiments, the pharmaceutical compositions comprise two different drug agents. Any combination of any two types of neuroprotective agents outlined herein is possible. In some cases, three neuroprotective agents can be combined for treatment.

In one embodiment, the pharmaceutical composition comprises two different MTMAs; for example, noscapine and a cannabinoid, including an endocannabinoid, find use in this embodiment.

In alternative embodiments, the pharmaceutical compositions comprise an MTMA and a neuroprotective agent that is not an MTMA.

In one embodiment, the neuroprotective agent is a voltage gated ion channel antagonist, including voltage gated sodium and calcium channel antagonists. Thus, compositions comprising at least one MTMA and a channel antagonist find particular use.

In many embodiments, the pharmaceutical compositions comprise an MTMA and an NMDA receptor antagonist. Compositions comprising noscapine and dizolcipine find particular use in some embodiments. In alternative embodiments, the NMDA receptor antagonist is Memamtine.

In many embodiments, the pharmaceutical compositions comprise an MTMA and a peroxisome proliferator-activated receptor gamma (PPARγ) agonist. Compositions comprising noscapine and pioglitazone (Actos®) find particular use in some embodiments. In alternative embodiments, the PPARγ agonist can be Rosiglitazone (Avandia®), L-796449, RS5444, or G1262570 among others.

In many embodiments, the pharmaceutical composition comprises MTMA and an anti-inflammatory agent, such as Celastrol, Nimesulide or Ibuprofen.

In many embodiments, the pharmaceutical compositions comprise an MTMA and an antioxidant, particularly iNOS antioxidants. Compositions comprising noscapine and L-NMMA (Tilarginine) find particular use in some embodiments. In alternative embodiments, the antioxidant can be chosen from Ceftriaxone, Celastrol, CoQ10, Vitamin E, or AEOL 10150 among others.

In many embodiments, the pharmaceutical compositions comprise an MTMA and a free radical trapper/scavenger. Compositions comprising noscapine and manganoporphyrin antioxidant among others find use in some embodiments.

In many embodiments, the pharmaceutical compositions comprise an MTMA and a metal ion chelator, particularly copper(II) and zinc(II) chelators. Compositions comprising noscapine and a metal ion chelator such as 8-hydroxyquinoline; acetohydroxamic acid; or N,N-dimethyl-2,3-dihydroxybenzamide (DMB), among others, find use in some embodiments.

In many embodiments, the pharmaceutical compositions comprise an MTMA and a low-voltage sensitive calcium channel (L-VSCCs) antagonist. Compositions comprising noscapine and Nimodipine find particular use in some embodiments.

In many embodiments, the pharmaceutical compositions comprise an MTMA and a noncompetitive α-amino-3-hydroxy-5-methylisoxazole-4-propionic acid (AMPA)/kainate receptor antagonist. Compositions comprising noscapine and GYKI 52466 find particular use in some embodiments.

In many embodiments, the pharmaceutical compositions comprise an MTMA and a selective or nonselective glutamate receptor antagonist. Compositions comprising noscapine and the nonselective glutamate receptor antagonist Sosei 51 (NC-1200/MVL-6976) find particular use in some embodiments. In alternative embodiments, the selective or nonselective glutamate receptor antagonist can be chosen from NBQX, Nimesuldine, Riluzole (Rilutek), Talampanel, Ceftriaxone, or Naaladase inhibitor. In other embodiments, the glutamate receptor antagonist may be a glial modulator such as ONO-2506.

In many embodiments, the pharmaceutical compositions comprise an MTMA and an Anandamide (AEA) transport, hydrolysis or reuptake inhibitor. Compositions comprising noscapine and N-(4-hydroxyphenyl)-arachidonamide (AM404) find particular use in some embodiments. In alternative embodiments, the AEA transport, hydrolysis or reuptake inhibitor may be N-(5Z,8Z,11Z,14Zeicosatetraenyl)-4-hydroxybenzamide (AM 1172) or a fatty acid amidohydrolase FAAH inhibitor, such as URB597. In addition, compositions comprising two MTMAs and an AEA reuptake inhibitor are also useful, such as noscapine, AEA and AM404.

In many embodiments, the pharmaceutical compositions comprise an MTMA and a neurotrophic factor. Compositions comprising noscapine and IGF1 or IGF-1-AAV find use in some embodiments.

In many embodiments, the pharmaceutical compositions comprise an MTMA and an apoptosis inhibitor. Compositions comprising noscapine and Minocycline, TCH346 or Tamoxifen may find use in some embodiments.

In some embodiments, two MTMAs are used as well as an additional neuroprotective agent.

By "motoneuron related disorder" or "motoneuron disease" or "condition" herein is meant a disorder that can be ameliorated by the administration of a pharmaceutical composition comprising two neuroprotective agents, typically comprising at least one MTMA, although one and more than two neuroprotective agents are also contemplated. In a particularly useful embodiment, the microtubule target modulating agent is used to treat amyotrophic lateral sclerosis (ALS).

In many embodiments, a therapeutically effective dose of neuroprotective agents is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a particularly useful embodiment, dosages of about 5 .mu.g/kg are used, administered either intravenously or subcutaneously. As is known in the art, adjustments for agent degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In a particularly useful embodiment the patient is a mammal, and in an especially useful embodiment the patient is human.

The term "treatment" in the instant invention is meant to include therapeutic treatment, as well as prophylactic, or suppressive measures for the disease or disorder. Thus, for example, in the case of motoneuron disease, successful administration of two neuroprotective agents, typically comprising at least one MTMA, although one and more than two neuroprotective agents are also contemplated, prior to the onset of the disease results in "treatment" of the disease. As another example, successful administration of the neuroprotective agents after clinical manifestation of the disease to combat the symptoms of the disease comprises "treatment" of the disease. "Treatment" also encompasses administration of the neuroprotective agents after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

As the compositions of the invention are typically combinations of at least two neuroprotective agents, the compositions can be administered together in a single dosage form (e.g., oral formulations that combine the two drugs) or singly, in any of the dosage forms outlined below, simultaneously or sequentially. For example, one drug can be administered orally and another intraperitoneally, either together or sequentially. In addition, when dosed separately, the dosages may be at different times or frequencies. Alternatively, at least two drugs may be administered separately but in the same dosage form, e.g., by oral administration.

Initial dosages suitable for administration to humans may be determined from in vitro assays or animal models. For example, an initial dosage may be formulated to achieve a serum concentration that includes the $IC_{50}$ of the particular metabolically active agent of the compound(s) being administered, as measured in an in vitro assay. Alternatively, an initial dosage for humans may be based upon dosages found to be effective in animal models of ALS, such as the SOD mouse. As one example, the initial dosage for each component of the pharmaceutical compositions outlined herein may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the compound(s) being employed. The size of the dose also will be determined by the existence, nature, and extent of any adverse side-effects that accompany the administration of a particular compound(s) in a particular patient. Determination of the proper dosage for a particular situation is within the skill of the practitioner. Generally, treatment is initiated with smaller dosages which are less than the optimum dose of the compound(s). Thereafter, the dosage is increased by small increments until the optimum effect under circumstances is reached. For convenience, the total daily dosage may be divided and administered in portions during the day, if desired.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Formulations suitable for oral administration can consist of (a) liquid solutions, such as an effective amount of the compound(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The active compound or pharmaceutically acceptable salt thereof can be administered as a component of an elixir, suspension, syrup, wafer, chewing gum or the like. Syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action.

As used herein, the term "pharmaceutically acceptable salt(s)" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counter-ion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The compound(s) of choice, alone or in combination with other suitable components, may be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged compound(s) with a suppository base. Suitable suppository bases include natural or synthetic triglycerides or paraffin hydrocarbons. In addition, it is also possible to use gelatin rectal capsules which consist of a combination of the compound(s) of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are particularly useful methods of administration. A specific example of a suitable solution formulation may comprise from about 0.1-100 mg/ml compound(s) and about 1000 mg/ml propylene glycol in water. Another specific example of a suitable solution formulation may comprise from about 0.1 or about 0.2 to about 100 mg/ml compound(s) and from about 800-1000 mg/ml polyethylene glycol 400 (PEG 400) in water.

A specific example of a suitable suspension formulation may include from about 0.2-30 mg/ml compound(s) and one or more excipients selected from the group consisting of: about 200 mg/ml ethanol, about 1000 mg/ml vegetable oil (e.g., corn oil), about 600-1000 mg/ml fruit juice (e.g., grape juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound(s), about 100-200 mg/ml lecithin (or other phospholipid or mixture of phospholipids) and optionally about 5 mg/ml cholesterol in water. For subcutaneous administration of a compound(s), a liposome suspension formulation including mg/ml compound(s) in water with 100 mg/ml lecithin and 5 mg/ml compound(s) in water with 100 mg/ml lecithin and 5 mg/ml cholesterol provides good results.

The formulations of compound(s) can be presented in unit-dose or multi-dose sealed containers, such as ampoules and vials. Injection solutions and suspensions can be prepared from sterile powders, granules, and tablets of the kind previously described.

The pharmaceutical preparation is particularly useful in unit dosage form. In such form the preparation is subdivided into unit doses containing appropriate quantities of the compound(s). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Mountain View, Calif.) and Gilford Pharmaceuticals (Baltimore, Md.). Liposomal suspensions also may be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidylcholine, arachadoyl phosphatidylcholine, and cholesterol) in an inorganic solvent that is then evaporated, leaving behind a thin film of dried lipid on the surface of the container. Aqueous solutions of the active compound or its derivatives are then introduced into the container. The container is then swirled by hand to free lipid material from the sides of the container and to disperse lipid aggregates, thereby forming the liposomal suspension.

Diagnosis of Motoneuron Diseases and Monitoring of Drug Activity in Subjects and in Clinical Trials In one embodiment, the methods of the invention allow the early diagnosis of motoneuron diseases, due to the use of the biochemical markers outlined herein, that allow the detection of motoneuron disease prior to onset of symptoms. Thus, by utilizing the methods of the invention, and detecting, for example, excess dynamicity (e.g., instability, high turnover rate) in the hillock and axonal shaft (STOP) microtubules, the presence of a motoneuron disease such as ALS can be detected. As generally the axonal microtubules are very stable (essentially no tubulin exchange over standard assay times), "instability" in this context is an increase in the percentage of new tubulin incorporation into motoneuron microtubules.

In a related embodiment, the methods of the present invention allow for monitoring of the response of an individual subject with motoneuron disease to a therapeutic intervention by detecting, for example, a change in the dynamicity of hillock and axonal shaft microtubules.

In another related embodiment, the methods of the present invention allow for the evaluation of efficacy of a candidate drug being tested in a clinical trial as a treatment for motoneuron disease. The change in dynamicity of hillock and axonal shaft microtubules, for example, during treatment with a candidate therapeutic agent can be evaluated in treated groups and compared statistically to determine biochemical efficacy of treatment regimens.

Drug Discovery and Development

Figure 13:
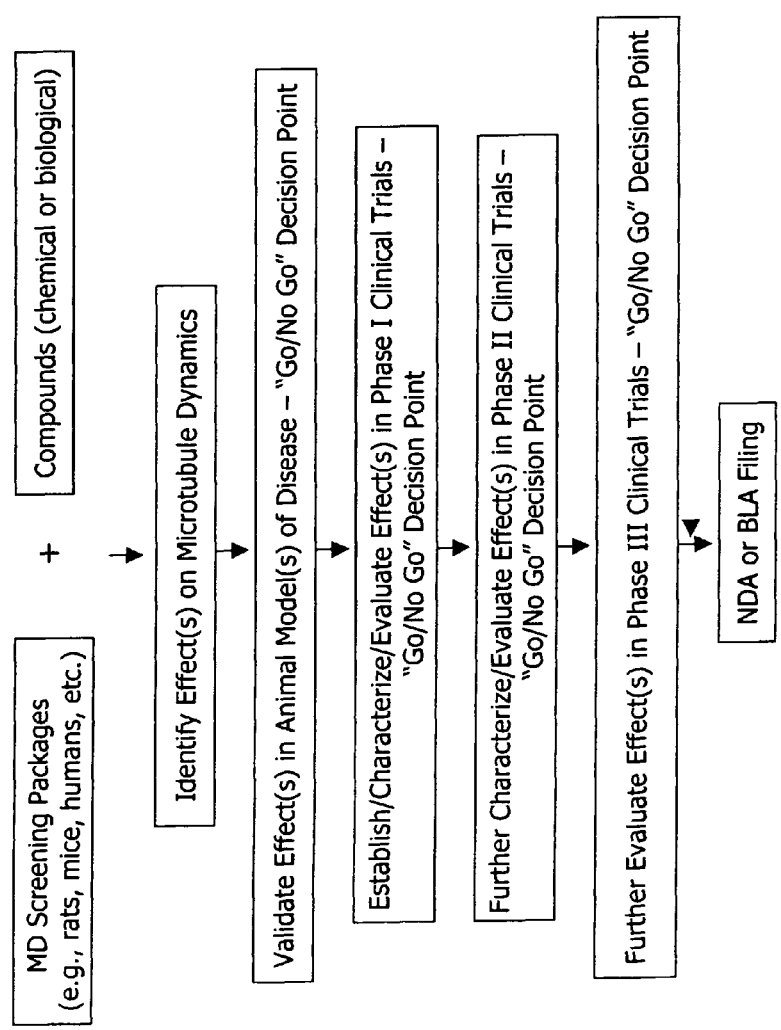
FIG. 13 is a schematic diagram showing the drug discovery, development, and approval (DDDA) process using effects on neuronal microtubule dynamics (i.e., data collected by the methods of the present invention) as a means for deciding to continue or cease efforts.

In one embodiment, the methods allow for assessing effects on microtubule dynamicity to be observed after a living system is exposed to a compound or combinations of compounds. The data generated and analyzed is therefore useful in the drug discovery, development, and approval (DDDA) process as it facilitates the DDDA decision-making process; i.e., it provides useful information for decision-makers in their decision to continue with further development on a compound or combination of compounds (e.g., if the microtubule dynamicity stabilization data appear promising) or to cease said efforts, for example, if the microtubule dynamicity stabilization data appear unfavorable (see FIG. 13 for a graphical depiction of this process).

Moreover, the methods allow for the skilled artisan to identify, select, and/or characterize "best in breed" in a class of compounds (I.e., "best in class"). Once identified, selected, and/or characterized, the skilled artisan, based on the information generated by the methods of the present invention, can decide to evaluate the "best in breed" further or to license the compound to another entity such as a pharmaceutical company or biotechnology company (see FIG. 14).

Figure 14:
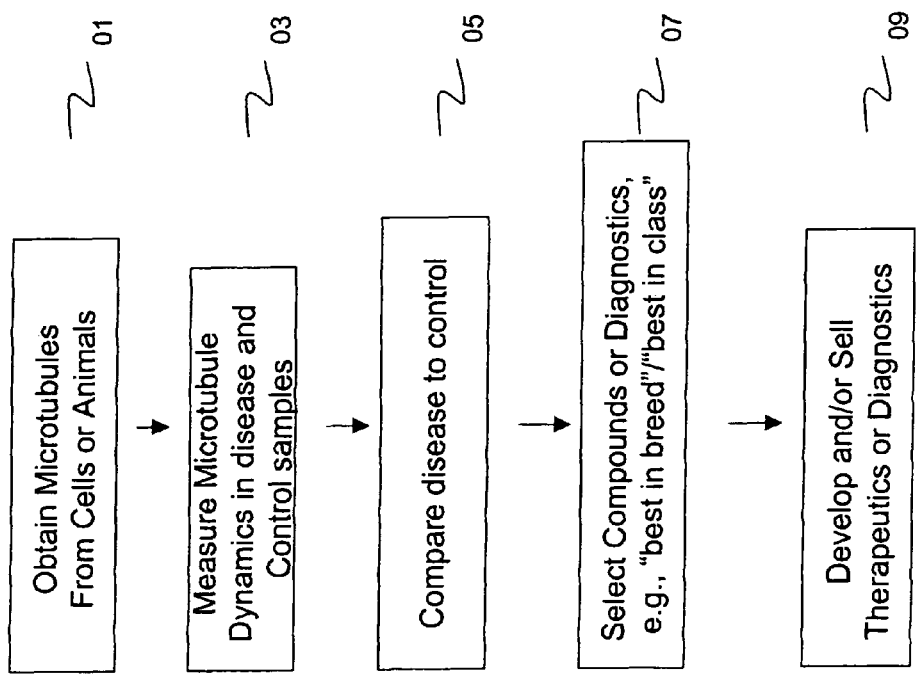
FIG. 14 illustrates use of the present invention in a drug discovery process.
Figure 15:
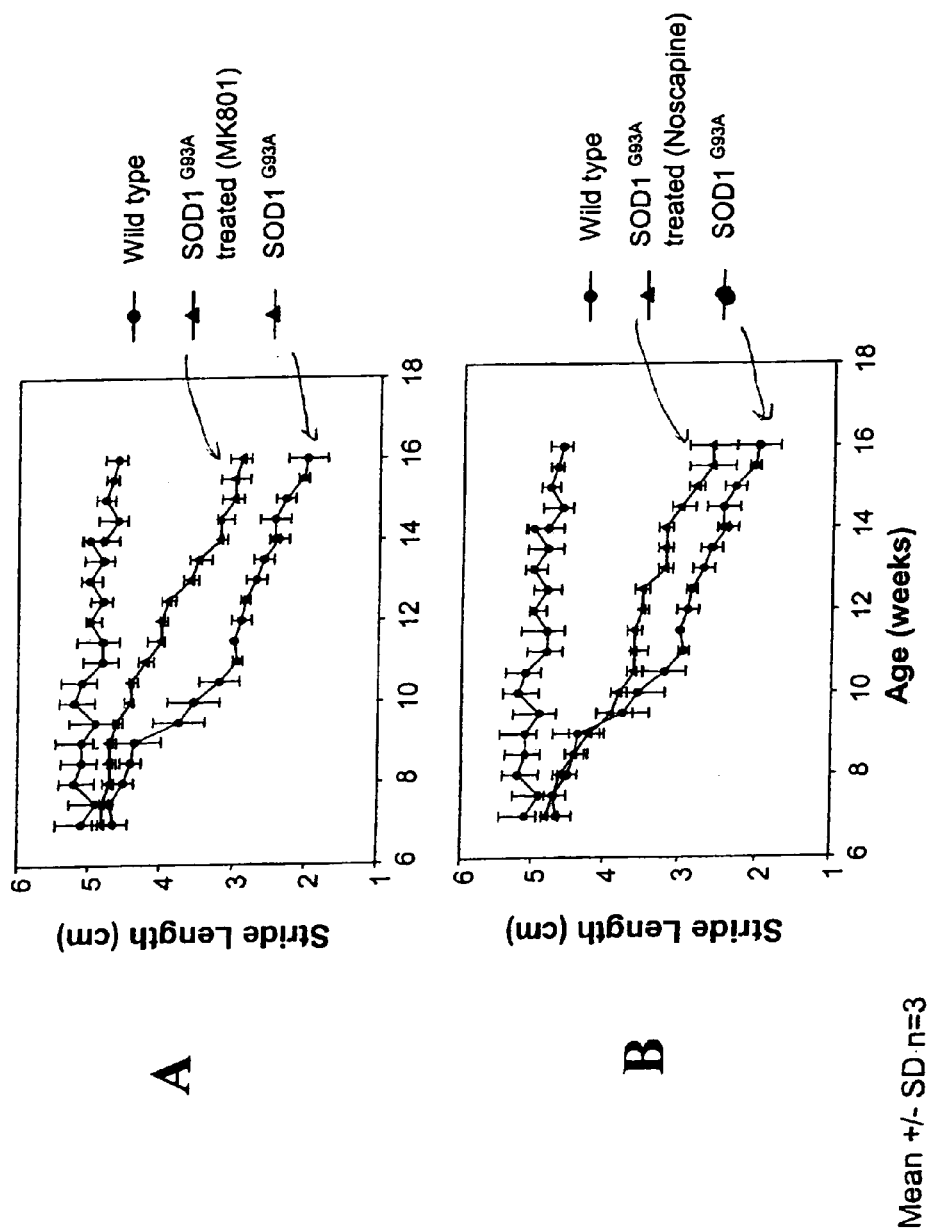
FIG. 15 shows the results of administering noscapine alone and MK801 alone.

FIG. 14 illustrates the use of the inventions herein in a drug discovery process. At step 01 a plurality of candidate agents are selected. At step 03 microtubule dynamicity is studied within cells or whole animals, usually according to the methods discussed herein. In alternative embodiments, step 03 is conducted first when the inventions are used, for example, in a target discovery process. At step 05 relevant microtubule dynamics data are identified. For example, if it is desirable to reduce microtubule dynamicity, a compound that reduces that dynamicity will be considered generally more useful, and conversely a compound that increases that dynamicity will be considered generally less desirable. In a target discovery process, a particular phenotype that has increased or decreased microtubule dynamicity with respect to another phenotype (e.g., diseased vs. not diseased or control) may be considered a good therapeutic or diagnostic target or in the pathway of a good therapeutic or diagnostic target. At step 07 compounds of interest, targets of interest, or diagnostics are selected and further used and further developed. In the case of targets, such targets may be the subject of, for example, well known small molecule screening processes (e.g., high-throughput screening of new chemical entities) and the like. Alternatively, biological factors, or already-approved drugs, or other candidate agents (or combinations and/or mixtures of candidate agents) may be used. At step 09 the compounds or diagnostics are sold or distributed. What is sold or distributed may be "best in breed," so identified by the methods of the present invention. It is recognized of course that one or more of the steps in the process in FIG. 14 will be repeated many times in most cases for optimal results.

EXAMPLES

Example 1

Isolation of Tubulin Dimers and Polymers

Tubulin was purified using minor modifications of protocols described previously (Fanara, P., Oback, B., Ashman, K., Podtelejnikov, A., Brandt, R. Identification of MINUS, a small polypeptide that functions as a microtubule nucleation suppressor. *EMBO J.* 18, 565-577 (1999); Fanara, P. et al. In vivo measurement of microtubule dynamics using stable isotope labeling with heavy water. Effect of taxanes. *J. Biol. Chem.* 279, 49940-49947 (2004). For purification ex vivo, mice were anesthetized with isoflurane and euthanized by cervical dislocation. Sciatic nerve was dissected and isolated as follows. The skin was pulled back to expose the muscle over the lower half of the body. Using scissors, the spinal cord was transected just below the lumbar region, and just above the wider sacral area. The partly opened scissors was slid down the lumbar region of the back bone, until the scissors hit at about the wide iliac portion of the hips. This cuts the sciatic nerve as close as possible to the spinal cord. Using forceps the muscle layer was lifted over the thigh portion (femur) of the leg. Then, the superficial layer of muscle was carefully cut to expose the white nerve in between muscle layers. The muscle over the nerve was transected and incisions were extended toward the foot and the hip. At the hip, the nerve turns and descends into the pelvic bone. The tip of the small scissors was slid into the muscle, parallel to the backbone and toward the first spinal cord cut. This exposed the last section of sciatic nerve (growth cone at the neuromuscular junction). Using the forceps, the white nerve was clutched and lifted. Smaller scissors were used to cut the few attachments left to the muscle. Tissue was then placed immediately into a tube and gently homogenized in MSB. To separate cytosolic tubulin dimers from microtubule polymers, post-nuclear supernatants were centrifuged at 190,000×g at 20° C. for 35 min. The supernatant or non-microtubule fraction (containing the soluble dimeric tubulin) was separated from the pellet or microtubule fraction (containing polymeric tubulin), quick-frozen and stored at −20° C. Microtubule pellets were further fractionated by sequential immunoaffinity chromatography steps. In order to isolate tau-associated microtubules, TAU5 antibody was covalently coupled to epoxy-activated Sepharose beads (Amersham Pharmacia Biotech) at a concentration of 0.25 mg/ml. Approximately 0.2 mg of the microtubule pellet was incubated with TAU-5 beads in 0.5 ml MSB for 1 hour at room temperature. Unbound material was removed, the beads were washed three times in 0.5 ml of MSB, and bound material was eluted in 0.5 ml MSB containing 1M NaCl. In some experiments, MAP2-associated microtubules were captured from the TAU5-unbound material by immunoaffinity chromatography on epoxy-activated Sepharose beads coupled to MAP2 antibody (0.5 mg antibody per ml beads) using the same protocol. The relative abundance of tubulin in each preparation (Tubulin dimers and TAU5-bound, MAP2-bound, and unbound microtubule fractions) was quantified by Western blot, and tubulin from these fractions was further purified by ion exchange and size exclusion chromatography, as previously described (Fanara, P. et al. In vivo measurement of microtubule dynamics using stable isotope labeling with heavy water. Effect of taxanes. *J. Biol. Chem.* 279, 499-4049947 (2004)).

Example 2

Isolation of Cold-Stable Microtubules

Cold-stable microtubules were isolated using minor modifications of protocols described previously (Pirollet, F., Derancourt, J., Haiech, J., Job, D., Margolis, R. L. Ca $(^{2+})$-calmodulin regulated effectors of microtubule stability in bovine brain. Biochemistry 31, 8849-8855 (1992)). Briefly, cell or tissue crude homogenates were prepared in ice-cold MSB (Fanara, P., Oback, B., Ashman, K., Podtelejnikov, A., Brandt, R. Identification of MINUS, a small polypeptide that functions as a microtubule nucleation suppressor. *EMBO J.* 18, 565-577 (1999) containing 1.5 mM $CaCl_2$, the proportion of buffer to cell mass or brain tissue was set at a ratio of 1.4:1 (vol/wt). After 2 min. on ice, EGTA was added to a final concentration of 3 mM, and the mixture was homogenized on ice for an additional 1 min. The extract was centrifuged at 150,000×g at 4° C. for 30 min, and the supernatant was collected. Microtubule assembly was initiated by incubating the supernatant at 30° C. After 1 h the extract was chilled at 4° C. for 20 min and centrifuged at 200,000×g for 30 min through a 50% (wt/vol) sucrose cushion in microtubule stabilizing buffer. After suspending the final pellet (cold-stable microtubules) in microtubule destabilizing buffer at 4° C., tubulin was purified as previously described (Fanara, P. et al. In vivo measurement of microtubule dynamics using stable isotope labeling with heavy water. Effect of taxanes. *J. Biol. Chem.* 279, 49940-49947 (2004)).

Example 3

Processing of Tubulin for GC/MS Analysis

Tubulin samples were hydrolyzed by treatment with 6N HCl for 16 hours at 110° C. Protein-derived amino acids were derivatized to pentafluorobenzyl derivatives, and 2H incorporation into alanine was measured by GC/MS as described in detail elsewhere (Fanara, P. et al. In vivo measurement of microtubule dynamics using stable isotope labeling with heavy water. Effect of taxanes. *J. Biol. Chem.* 279, 499-4049947 (2004)). $^2H$ enrichment was calculated as the percent increase, over natural abundance, in the percentage of alanine derivative present as the (M+1) mass isotopomer.

Example 4

Measurement of $^2H_2O$ Enrichment of in Body Water

Body water enrichment of $2H_2O$ enrichment and culture media was measured as described, supra. Briefly, protons from plasma water were transferred to acetylene by reaction with calcium carbide. Acetylene samples were then analyzed using a Series 3000 cycloidal mass spectrometer (Monitor Instruments, Cheswick, Pa.), which was modified to record ions at m/z 26 and 27 ($M_0$ and $M_1$) and calibrated against a standard curve prepared by mixing 99.9% $^2H_2O$ with unlabeled water. Body water 2H enrichments were not affected by drug treatment (data not shown).

Example 5

Noscapine-MK801 Treatment of SOD1-G93A TGN Mice

Female SOD-1 G93A TGN mice were obtained from Jackson laboratory (strain #2726). The controls were matched litter mates. Treatment groups were three per group. Noscapine was injected intraperitoneal in the thigh 3 times/week (0.2 mg/kg i.p.) and MK801 was administered continuously in drinking water (12 mg/kg/d). Gait analysis was done by the method of Wooley et al., Muscle Nerve 2005 32(1):43-50 and Carter et al. J. Neurosci., 19(8):3248-3257, hereby incorporated by reference in their entirety.

For clinical assessment endpoints scoring was selected as follows:
GROUP CLASSIFICATION: Presymptomatic
Clinical signs: Full mobility and no observable difference in behavior from age-matched controls (Gait or stride length analysis).
GROUP CLASSIFICATION: Onset
Clinical signs: Abnormal Gait or stride length analysis and hindlimb weakness: >40% reduction in stride length vs. age-matched littermates.
GROUP CLASSIFICATION: End Stage (euthanization)
Clinical signs: noticeable and complete hind limb paralysis (which in this strain occurs more on one limb than the other) and inability to right themselves in 5 sec time window. This stage starts usually as the mice are failing the gait analysis test and enter the End stage. Therefore, Transgenic SOD1-G93A TGN mice are euthanized at the onset of noticeable and complete hindlimb paralysis and inability to right themselves in 5 sec time window.

Untreated transgenic mice showed complete hind limb paralysis starting at 15 weeks of age, about 17 days after the disease onset, and were ultimately euthanized at 16 weeks of age (exhibiting the following symptoms: extensive paralysis, failure of pulling one limb for a full stride [scored as "0" on gait analysis] and inability to right themselves in 5 sec time window).

One of the treated mice showed complete hind limb paralysis starting at 16 weeks of age, 25 days after the disease onset, and was ultimately euthanized at 17 weeks of age (exhibiting the following symptoms: extensive paralysis, failure of pulling one limb for a full stride [scored as "0" on gait analysis] and inability to right itself in 5 sec time window).

The other 2 treated transgenic mice started to develop hind limb weakness (as scored by gait analysis) at roughly 18 weeks of age, however they had not yet developed noticeable and complete hind limb paralysis at that time.

TABLE 1

| Group | Onset to Death |
| --- | --- |
| SOD1-G93A TGN untreated (control group) | 17 days (average) |
| SOD1-G93A TGN treated with combination | ~38 days |

To compare, Riluzole ALS treatment previously studied in the ALS SOD1 G93A mouse and published by ALS TDF or other researchers:

| Group | Onset to Death |
| --- | --- |
| SOD1-G93A TGN untreated (control group) | 10-12 days |
| SOD1-G93A TGN treated with Riluzole | 14-20 days |

Onset of Motor Deficits and Mortality of SOD1-G93A TGN Mice Treated with Noscapine and/or MK-801:

| | Vehicle 20% cyclo-dextran | MK-801 | Noscapine | MK-801 + Noscapine |
| --- | --- | --- | --- | --- |
| Onset | 88-100 days | 105-112 days | 98-105 days | 119-126 days |
| Mortality | 105-112 days | 112-119 days | 112-119 days | 125-140 days |

Example 6

Therapeutic Interventions in Symptomatic SOD1$^{G93A}$ Mice

Figure 16:
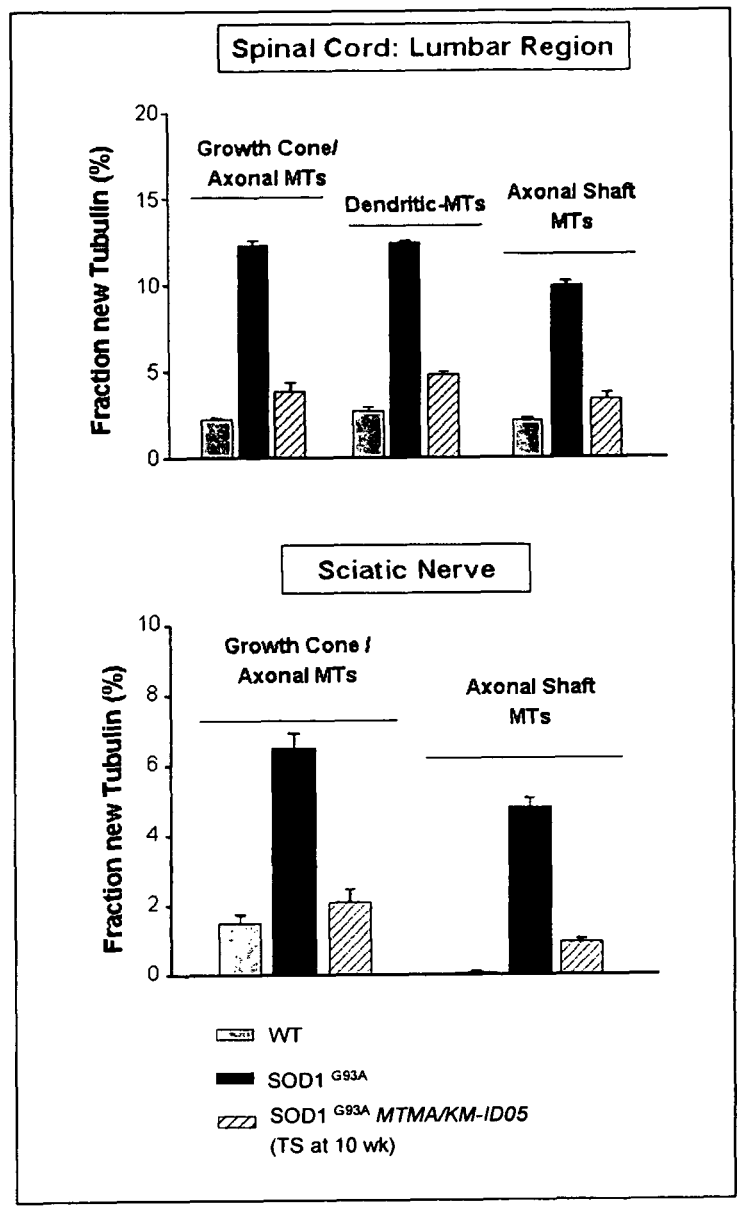
FIG. 16. MTMA/KM-ID05 potently reduces hyperdynamic microtubule in central nervous system (CNS) and peripheral nervous system (PNS) of 13 week old $SOD1^{G93A}$ mice (n=3; mean±SD).

A successful identification of novel two-drug therapy is shown in FIG. 16. The MTMA/KM-ID05 drug was administered to symptomatic SOD1$^{G93A}$ mice (10 weeks) and treatment was carried out for 3 weeks (n=3). $^2H_2O$ (8%) was administered in the last 2 days of treatment and mice were sacrificed after 48 hours of labeling. Lumbar region of spinal cord (between L2 and L5 levels) and the whole length of the sciatic nerve were dissected out and carefully removed. Microtubule dynamics was measured in all neuronal compartments of spinal motor neuron and sciatic nerve.

As detailed in FIG. 16, MTMA/KM-ID05 treated SOD1$^{G93A}$ mice showed significant reduction of hyperdynamic microtubules, down to levels close to that of the wild type mice. The positive effect of MTMA/KM-ID05 was detected in all neuronal compartments.

Figure 17:
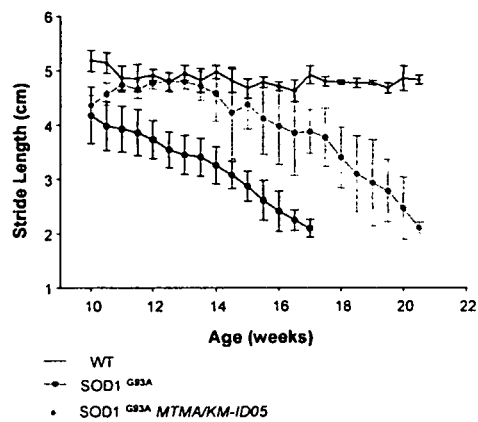
FIG. 17. MTMA/KM-ID05 improved locomotor activity and delayed disease onset in $SOD1^{G93A}$ mice. Treatment started at symptomatic phase (at age 10 weeks). Mice were scored for locomotor activity abnormality using stride length measurements (n=20; mean±SD).

To determine the effects of MTMA/KM-ID05 on disease progression in SOD1$^{G93A}$ mice, we conducted stride length measurements (FIG. 17). Stride length was determined by painting the paws with glycerol tinted with food coloring. The test was repeated until a mouse walked in a straight line and four clear continuous stride-length measurements could be obtained. Stride length is the distance between prints made by the same paw, taken from the center of one print to the center of the next.

The analysis was carried out always at the same time of the day, using age-matched transgenic untreated, treated and control animals of same gender (n=20). Unlike control mice, the SOD1$^{G93A}$ mice exhibited an age-dependent decline in motor performance (FIG. 17). The onset of the disease in SOD1$^{G93A}$ mice was characterized by a 40% reduction in stride length (at age of 12.5 weeks), followed by a rapid decline stage that progressed to a stage of complete hind limb paralysis (17 weeks). Note that the two-drug treatment significantly delayed the onset of disease and improved the motor performance of the SOD1$^{G93A}$ mice throughout the test period (FIG. 17). MTMA/KM-ID05 also significantly decreased weight loss in SOD1$^{G93A}$ mice by 30% (data not shown).

To assess whether the MTMA/KM-ID05 treatment decreased degeneration of motor neurons, we counted the number of motor neurons in a segment of the sciatic motor pool of each spinal cord. The effect of treatment was assessed in 15 weeks old SOD1$^{G93A}$ mice.

Figure 18:
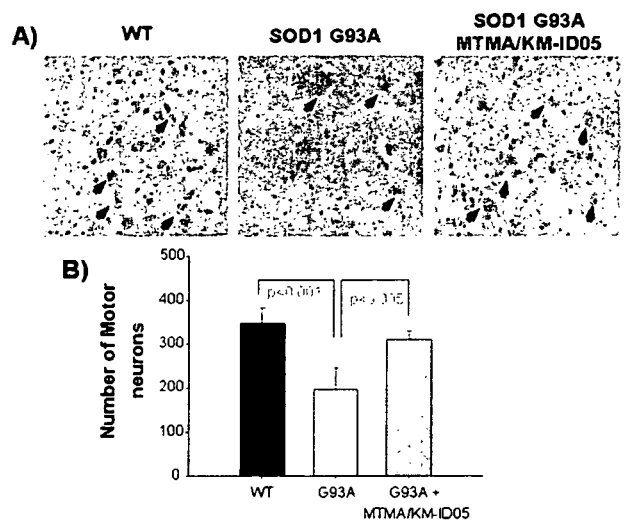
FIG. 18. The neuroprotective effect of treatment with MTMA/KM-ID05 in $SOD1^{G93A}$ mice at 15 weeks of age. (A) Spinal cord section stained for Nissl, showing motor neurons in the sciatic motor pool (arrowheads) of wilt type (WT) untreated and treated $SOD1^{G93A}$ mice. (B) Motor neuron survival in each experimental group (mean±SD).

An example of Nissl-stained spinal cord sections of wild type control (WT) untreated (SOD1$^{G93A}$) and treated (SOD1$^{G93A}$ MTMA/KM-ID05) mice is shown in FIG. 18A. The improvement in motor neuron survival observed in MTMA/KM-ID05 treated SOD1$^{G93A}$ mice was reflected in an increase in motor neuron survival, and the results are summarized in FIG. 18B. At the age of 15 weeks, a significant number of motor neurons in the sciatic pool had already died in untreated SOD1$^{G93A}$ mice, and only 197 (±10.2) motor neurons survived compared with 387 (±6.2) in WT littermate. However, treatment with MTMA/KM-ID05 rescued a significant portion of motor neurons, so that 298 (±4.4) motor neurons survived. Thus, in MTMA/KM-ID05 treated SOD1$^{G93A}$ mice, 50% more motor neurons survive even at 15 weeks compared with their untreated SOD1$^{G93A}$ littermates.

The effect of treatment with MTMA/KM-ID05 on the life span of SOD1$^{G93A}$ mice (n=20) was examined next. Untreated SOD1$^{G93A}$ mice live on average 118.5 (±4.2) days. End-stage in these experiments is determined by the age when the mice have lost 15% in their body weight, they exhibit full hind limb paralysis and lack of grooming, and they can no longer right themselves.

MTMA/KM-ID05 significantly extended survival of SOD1$^{G93A}$ mice by 25.6 days and increased life span by 22%.

In conclusion, when MTMA/KM-ID05 was administered at symptomatic stage it was able to potently reduce microtubule hyperdymanicity. Remarkably, the MTMA/KM-ID05 mechanism of action did ameliorate disease symptoms, which was reflected in a significant increase in motor neuron survival and life span of SOD1$^{G93A}$ mice.

Changes in slow axonal transport have been linked to the pathogenesis of mutant SOD1 transgenic mice. Slow axonal transport has previously been shown to have two components, based on rates of movement: one at ~0.5 mm/day the other at ~1-2 mm/day. Both components of transport include tubulin.

To determine whether the MTMA/KM-ID05 treatment can restore impaired axonal transport, we measured the rate of transport of $^2$H-labeled tubulin in the L5 root and sciatic nerve of SOD1$^{G93A}$ transgenic mouse. At the age of 13 weeks, a significant accumulation of 2H-tubulin is found in the L5 root, hillock and initial segment of proximal axons in untreated SOD1$^{G93A}$, compared with WT littermates. However, treatment with MTMA/KM-ID05 completely restored the rate of transport of $^2$H labeled tubulin along the axon to normal. Thus, in MTMA/KM-ID05 treated SOD1$^{G93A}$ mice, microtubule-based axonal transport is entirely restored compared to untreated SOD1$^{G93A}$ littermates.

Taken together, these results demonstrate that microtubule dynamics are a biomarker of disease activity. Accordingly, they can be used to evaluate new therapies and predict clinical efficacy in ALS.

Figure 19:
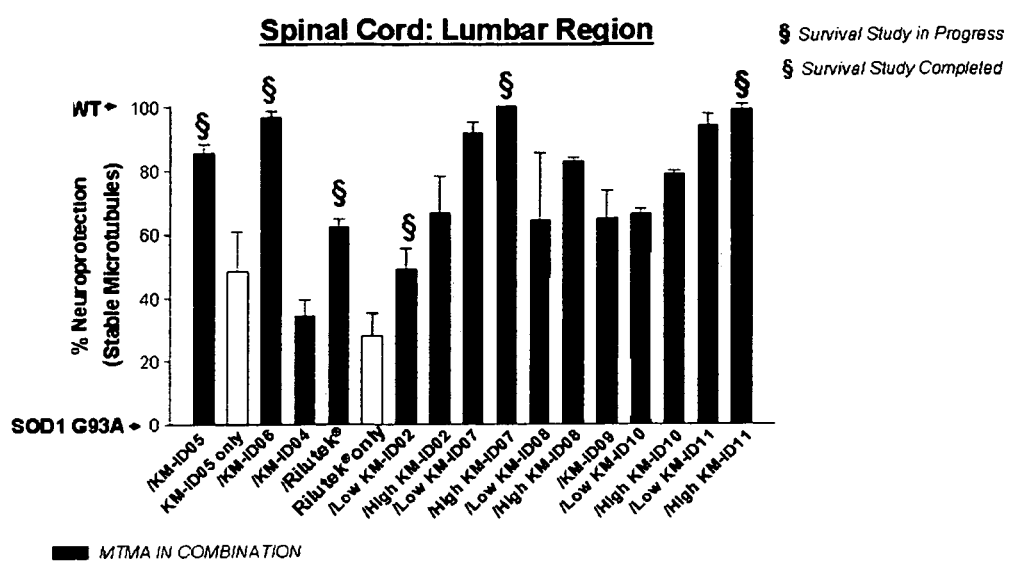
FIG. 19. The microtubule dynamics assay is used as a platform for pre-clinical drug discovery of novel therapeutic agents in symptomatic $SOD1^{G93A}$ mice. Neuroprotective activities were measured by comparing the ability of various agents to restore microtubule dynamics to the level observed in WT littermate. Percent neuroprotection was defined as the ability of agents to stabilize hyperdynamic microtubules of untreated $SOD1^{G93A}$ relative to WT littermate. Thus, higher values (up to 100%) represent higher neuroprotective activity. Treatments were all started in the symptomatic phase at age 10 weeks (n=3 mice/group). Mice were sacrifice after 3 weeks of treatment (age 13 weeks) to measure microtubule dynamics in the neuronal compartments of spinal motor neurons (average of all compartments shown here, as mean±SD).
Figure 20:
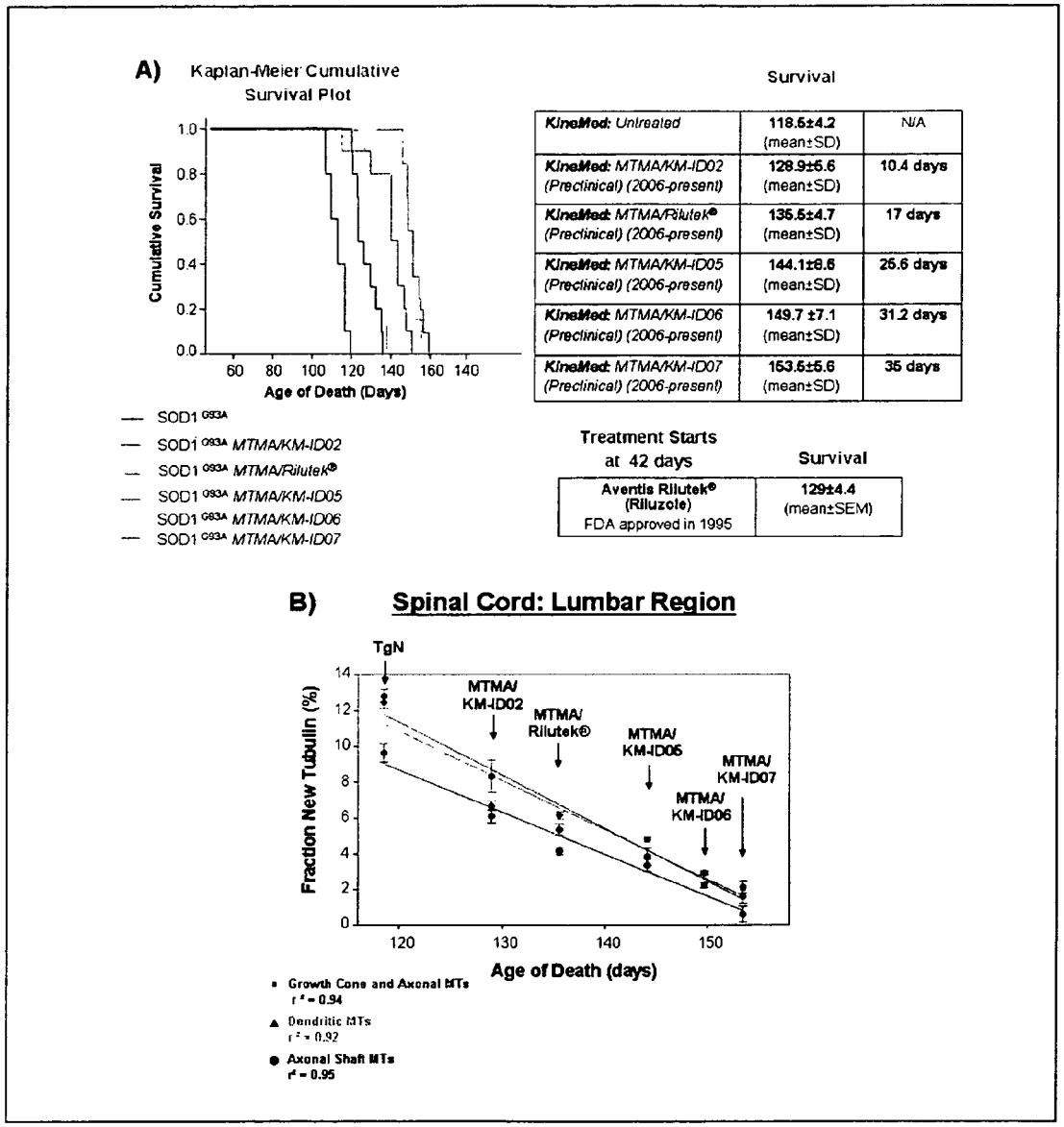
FIG. 20. (A) Survival plots and statistical analysis of survival for five neuroprotective candidate agents. (B) Biomarker predictivity graphed as microtubule dynamics versus survival outcome in $SOD1^{G93A}$ mice for different agents (mean±SD).
Figure 22:
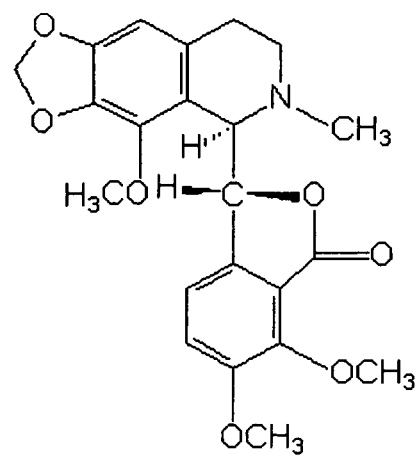
FIG. 22 depicts the structure of noscapine.

As detailed in FIG. 19, we used microtubule dynamics assay to assess and compare the relative neuroprotective activities of a number of candidate combination agents studied in vivo. Prediction of clinical efficacy between "potent" and "weak" neuroprotection was evaluated (FIG. 19). Five of the two-agent combinations were selected for further evaluation for efficacy in delaying disease progression and increasing survival of SOD1$^{G93A}$ mice (each group n=20 mice) (FIG. 20). Treated SOD1$^{G93A}$ mice experienced between a 10% to 32% increase in lifespan as a function of effectiveness in neuroprotection (microtubule stability). We documented a remarkably close correlation between the biochemical measure of microtubule dynamics in vivo and hard clinical outcomes (stride length and survival) (FIG. 20). These findings demonstrate microtubule dynamics to be a powerful ALS biomarker of disease activity and therapeutic response (FIG. 21).

We claim:

1. A method of treating a motoneuron disease in a patient wherein said motoneuron disease is selected from the group consisting of amyotrophic lateral sclerosis (ALS), diabetic neuropathy and Parkinson's disease comprising administering a pharmaceutical composition comprising a first microtubule target modulating agent (MTMA), wherein the first MTMA is noscapine.

2. A method according to claim 1 wherein the motoneuron disease is amyotrophic lateral sclerosis (ALS).

3. A method according to claim 1, further comprising administering to said patient a first neuroprotective agent selected from the group consisting of a voltage gated ion channel antagonist, a peroxisome proliferation-activated receptor γ (PPARγ), an antioxidant, an L-VSCCs antagonist, an α-amino-3-hydroxy-5-methyl-4-isoxazolepropionic acid (AMPA) antagonist, nonselective blocker of glutamate receptor, an anandamine (AEA) reuptake inhibitor, and a second MTMA.

4. A method according to claim 3, wherein when said first neuroprotective agent is a voltage gated ion channel antagonist, said first neuroprotective agent is a voltage gated calcium channel (VGCH) antagonist.

5. A method according to claim 4, wherein said VGCH antagonist is N-methyl-D-aspartate (NMDA) receptor antagonist.

6. A method according to claim 5, wherein said NMDA receptor antagonist is dizolcipine.

7. A method of treating a motoneuron disease in a patient wherein said motoneuron disease is selected from the group consisting of amyotrophic lateral sclerosis (ALS), diabetic neuropathy and Parkinson's disease comprising administering a pharmaceutical composition comprising a first microtubule target modulating agent (MTMA), wherein the first MTMA is a noscapine and N-methyl-D-aspartate (NMDA) receptor antagonist wherein said NMDA receptor antagonist is dizolcipine.

8. The method according to claim 7, wherein the motoneuron disease is ALS.

* * * * *